(12) United States Patent
Verma

(10) Patent No.: US 7,432,051 B2
(45) Date of Patent: Oct. 7, 2008

(54) ERYTHROPOIETIN AND ERYTHROPOIETIN RECEPTOR EXPRESSION IN HUMAN CANCER

(75) Inventor: Ajay Verma, Bethesda, MD (US)

(73) Assignee: The Henry M. Jackson Foundation for the Advancement of Military Medicine, Inc., Rockville, MD (US)

( * ) Notice: Subject to any disclaimer, the term of this patent is extended or adjusted under 35 U.S.C. 154(b) by 573 days.

(21) Appl. No.: 10/432,899

(22) PCT Filed: Nov. 30, 2001

(86) PCT No.: PCT/US01/44950

§ 371 (c)(1),
(2), (4) Date: Nov. 12, 2003

(87) PCT Pub. No.: WO02/43572

PCT Pub. Date: Jun. 6, 2002

(65) Prior Publication Data

US 2005/0260580 A1    Nov. 24, 2005

Related U.S. Application Data

(60) Provisional application No. 60/253,941, filed on Nov. 30, 2000.

(51) Int. Cl.
*C12Q 1/68* (2006.01)
*C07K 14/505* (2006.01)

(52) U.S. Cl. .......................... 435/6; 530/397

(58) Field of Classification Search ....................... None
See application file for complete search history.

(56) References Cited

U.S. PATENT DOCUMENTS 6,103,879 A    8/2000    Chaovapong et al. .... 530/388.1
6,310,078 B1   10/2001   Connolly et al. ............ 514/330

FOREIGN PATENT DOCUMENTS

WO    WO 00/61637    10/2000

OTHER PUBLICATIONS

Funakoshi et al., Gene expression of mutantn erythropoietin in hepatocellular carcinoma. Biochemical and Biophysical Research Communications, vol. 195, No. 2, pp. 717-722 (Sep. 15, 1993).*
Westenfelder et al. Erythropoietin stimulates proliferation of human renal carcinoma cells. Kidney International, vol. 58 pp. 647-657 (Aug. 2000).*
Horinouchi et al. Erythropoietin mRNA in hepatocellular carcinomas and kidney in male B6C3F1 mice with secondary polycythemia. Toxicologic Pathology, vol. 26, No. 5 pp. 682-686 (Sep.-Oct. 1998).*
Benyo et al. (1999) Expression of the erythropoietin receptor by trophoblast cells in the human placenta, Biol. Reprod. 60:861-870.
Brown (1999) The hypoxic cell: a target for selective cancer therapy—eighteenth Bruce F. Cain Memorial Award lecture, Cancer Res. 59:5863-5870.
Bunn et al. (1996) Oxygen sensing and molecular adaptation to hypoxia, Physiol. Rev. 76:839-885.
Cerami (2001) Beyond erythropoiesis: novel applications for recombinant human erythropoietin, Semin. Hematol. 38:33-39.
Cheung et al. (2001) Molecular mechanisms of erythropoietin signaling, Nephron. 87:215-222.
Diagicaylioglu et al. (2001) Erythropoietin-mediated neuroprotection involves cross-talk between Jak2 and NF-kappaB signalling cascades, Nature 412:641-647.
Graeber et al. (1996) Hypoxia-mediated selection of cells with diminshed apoptotic potential in solid tumours, Nature 379:88-91.
Jacobs et al. (1985) Isolation and characterization of genomic and cDNA clones of human erythropoietin, Nature 313:806-810.
Jones et al. (1990) Human erythropoietin receptor: cloning, expression, and biologic characterization, Blood 76:31-35.
Juul et al. (1999) Immunohistochemical localization of erythropoietin and its receptor in the developing human brain, Pediatr. Dev. Pathol. 2:148-158.
Juul et al. (1999) Why is erythropoietin present in human milk? Studies of erythropoietin receptors on enterocytes of human and rat neonates, Pediatr. Res. 46:263-268.
Kalra et al. (1993) The effect of hypoxia on acquired drug resistance and response epidermal growth factors in Chinese hamster lung fibroblasts and human breast-cancer cells in vitro, Int. J. Cancer 54:650-655.
Kling et al. (1998) Human milk as a potential enteral source of erythropoietin, Pediatr. Res. 43:216-221.
Marti et al. (1996) Erythropoietin gene expression in human, monkey and murine brain, Eur. J. Neurosci. 8:666-676.
Mitjavila et al. (1991) Autocrine stimulation by erythropoietin and autonomous growth of human erythroid leukemic cells in vitro, J. Clin. Invest. 88:789-797.
Sasaki et al. (2001) Pleiotropic functions and tissue-specific expression of erythropoietin, News Physiol. Sci. 16:110-113.
Schmatlz et al. (1998) Regulation of proliferation-survival decisions during tumor cell hypoxia, Mol. Cell Biol. 18:2845-2854.
Semenza (1999) Regulation of mammalian oxygen homeostasis by hypoxia-inducible factor 1, Annu. Rev. Cell Dev. Biol. 15:551-578.
Tachibana et al. (1991) Immunohistochemical study of erythropoietin in cerebellar hemangioblastomas associates with secodary polycythemia, Neurosurgery, 28:24-16.
Zagzag et al. (2000) Expression of hypoxia-inducible factor 1alpha in brain tumors: association with angiogenesis, invasions, and progression, Cancer 88:2606-2618.

* cited by examiner

*Primary Examiner*—Marianne P. Allen
*Assistant Examiner*—Regina M DeBerry
(74) *Attorney, Agent, or Firm*—Morgan, Lewis & Bockius LLP

(57) ABSTRACT

The present invention relates to the elucidation of the role of erythropoietin and the erythropoietin receptor in the development and progression of certain solid tumors, including those found in breast, cervical, uterine, ovarian, prostate and brain cancer.

8 Claims, 14 Drawing Sheets

Fig. 1
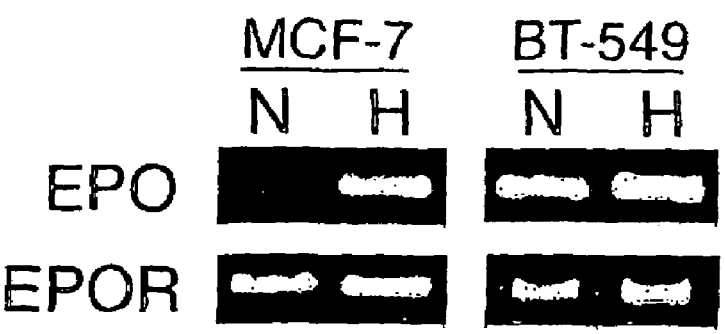
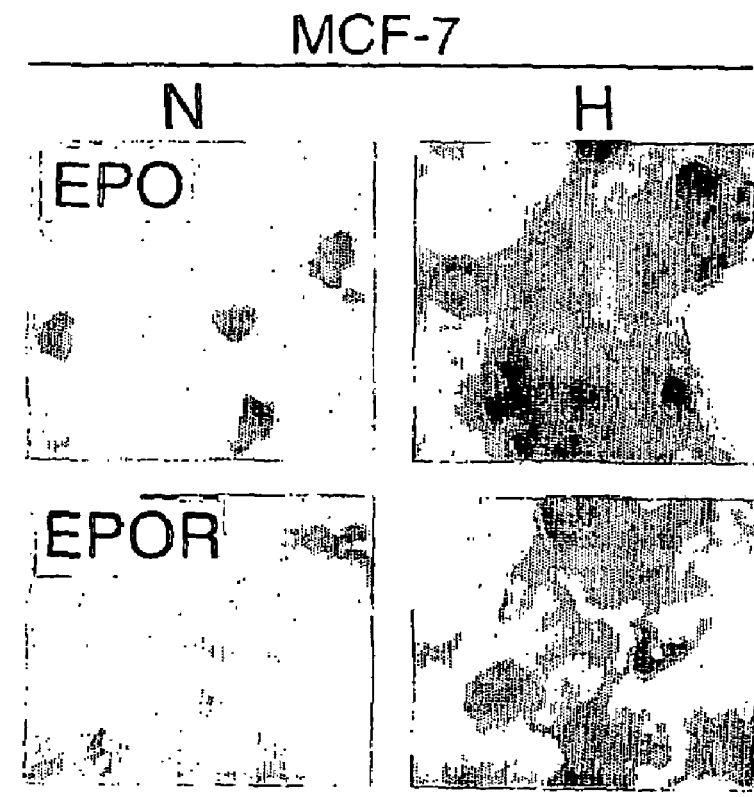

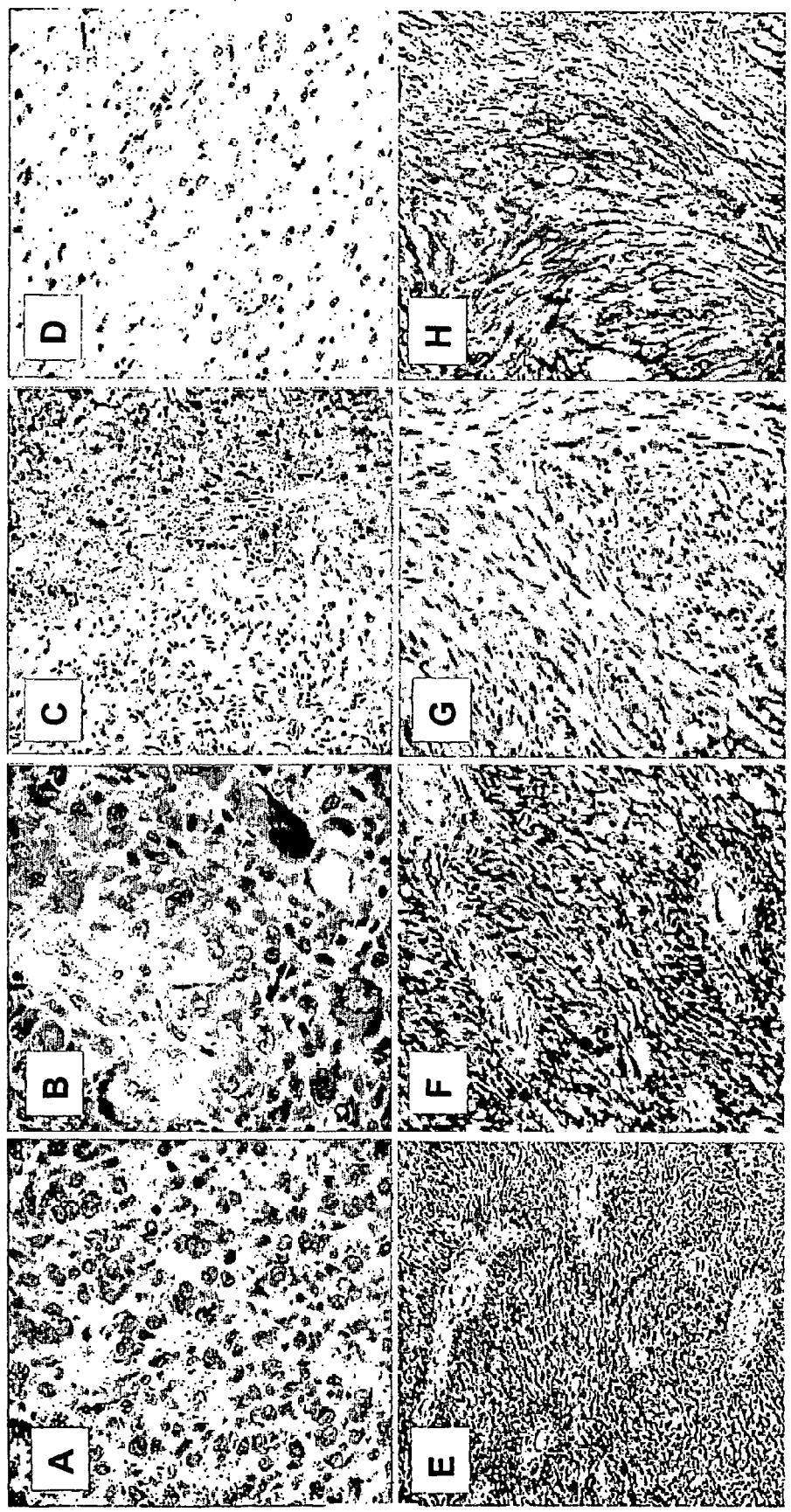
Figure 9A- EPOR Expression Patterns in Human Glioblastoma Multiforme

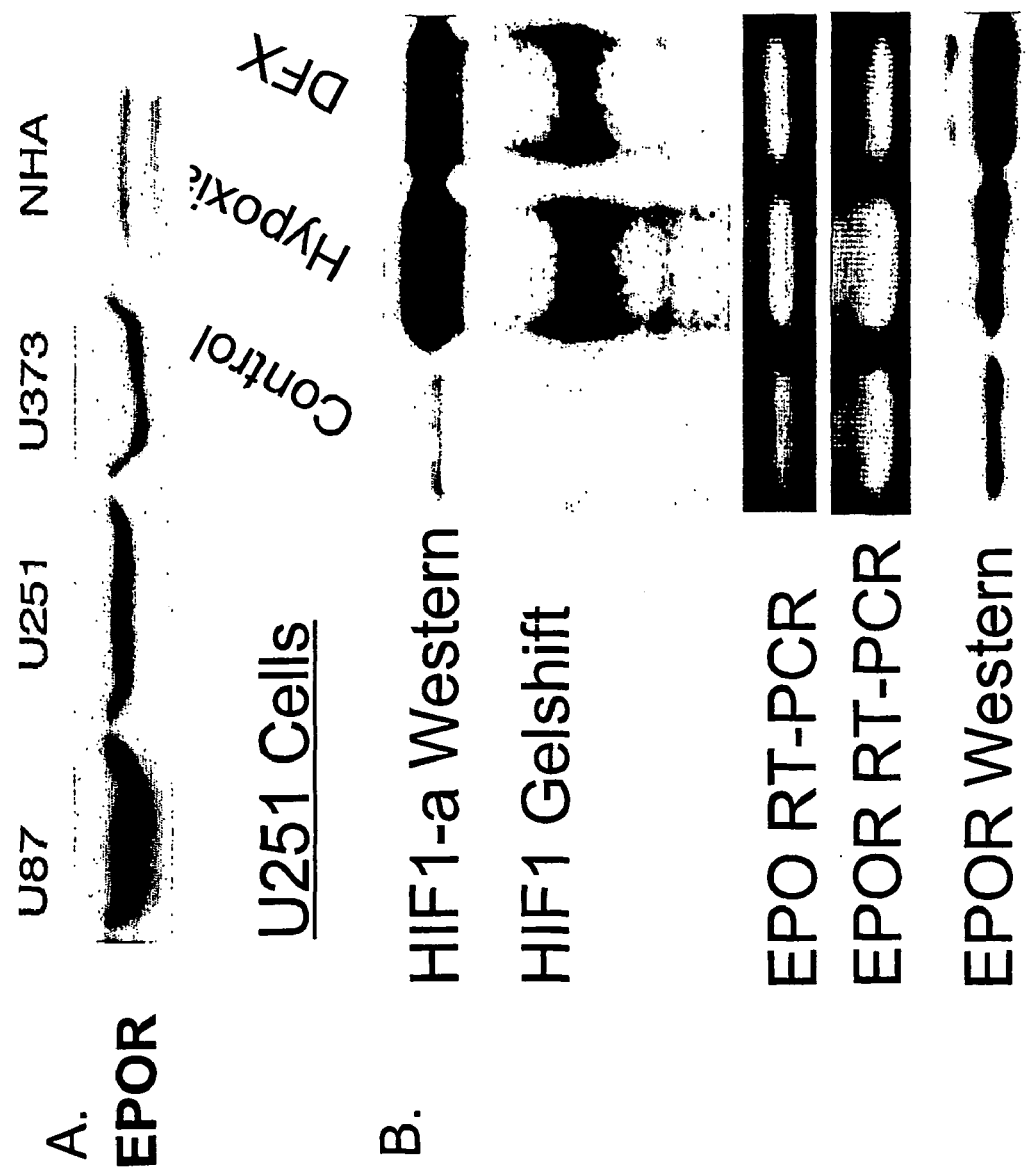
Figure 10- EPOR Expression in Gliomas is Enhanced by Hypoxia

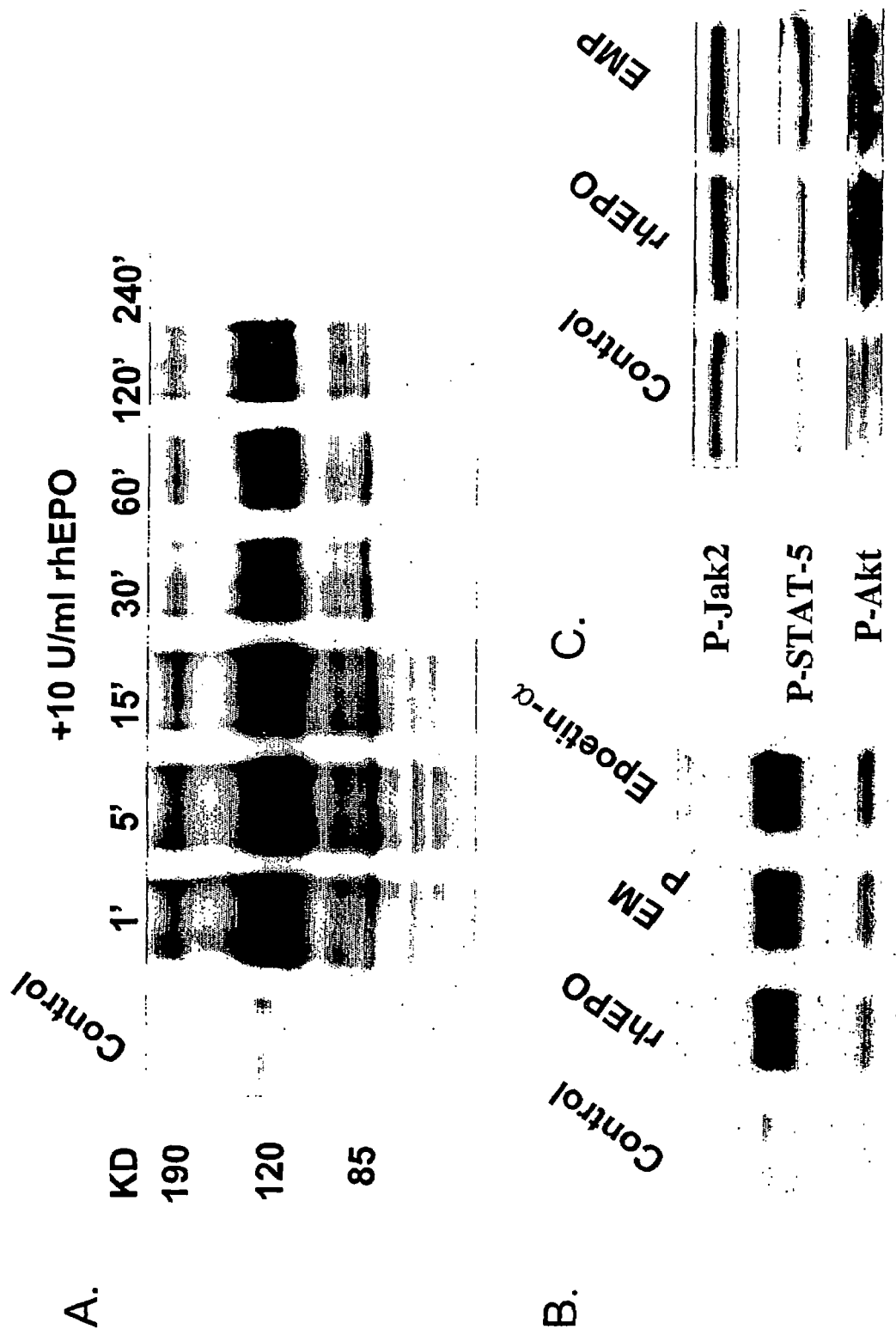
Figure 11- Erythropoietin Activates Signaling pathways in Gliomas

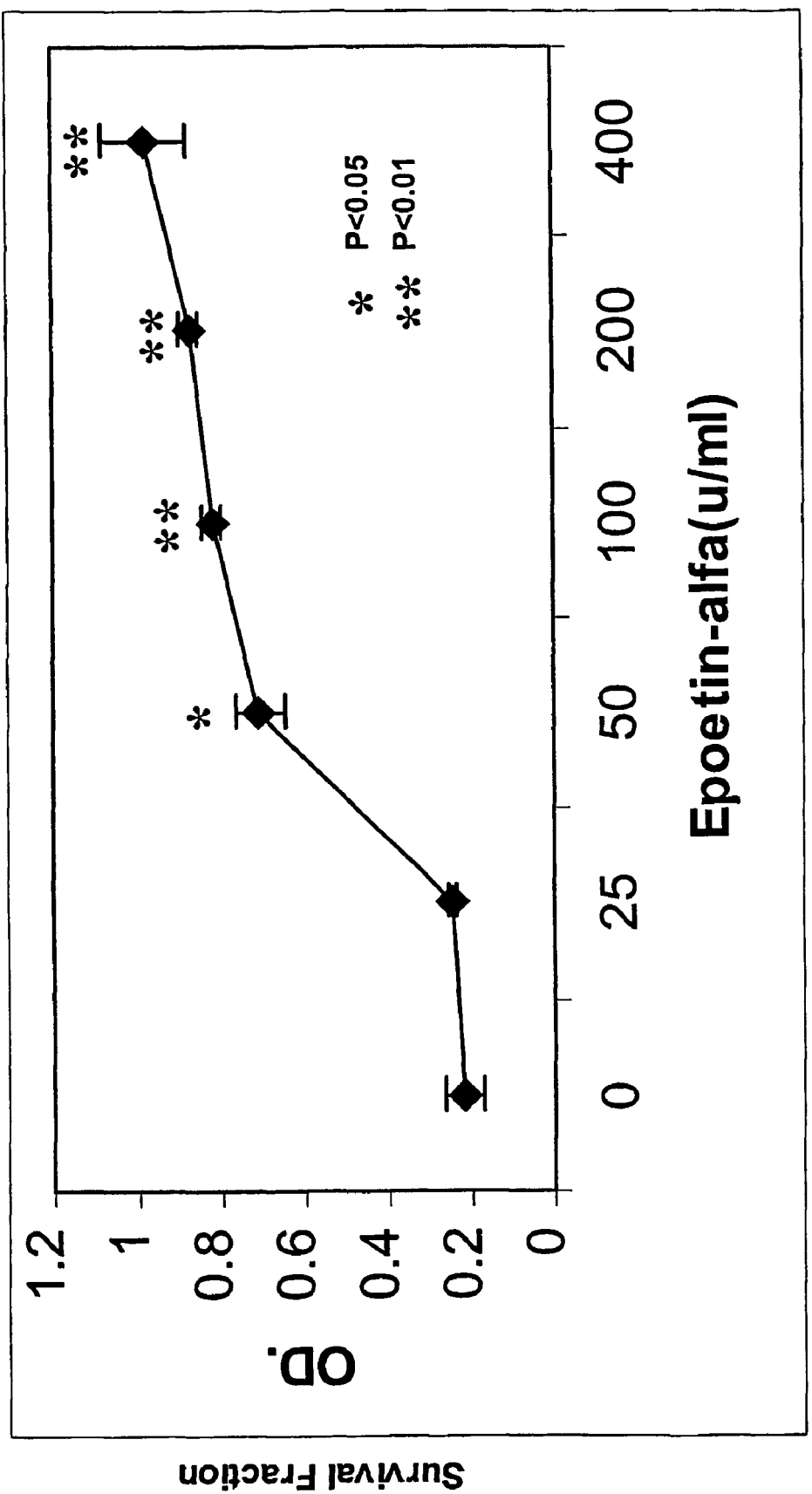
Figure 12- Erythropoietin Protects Gliomas Against Cisplatin Toxicity

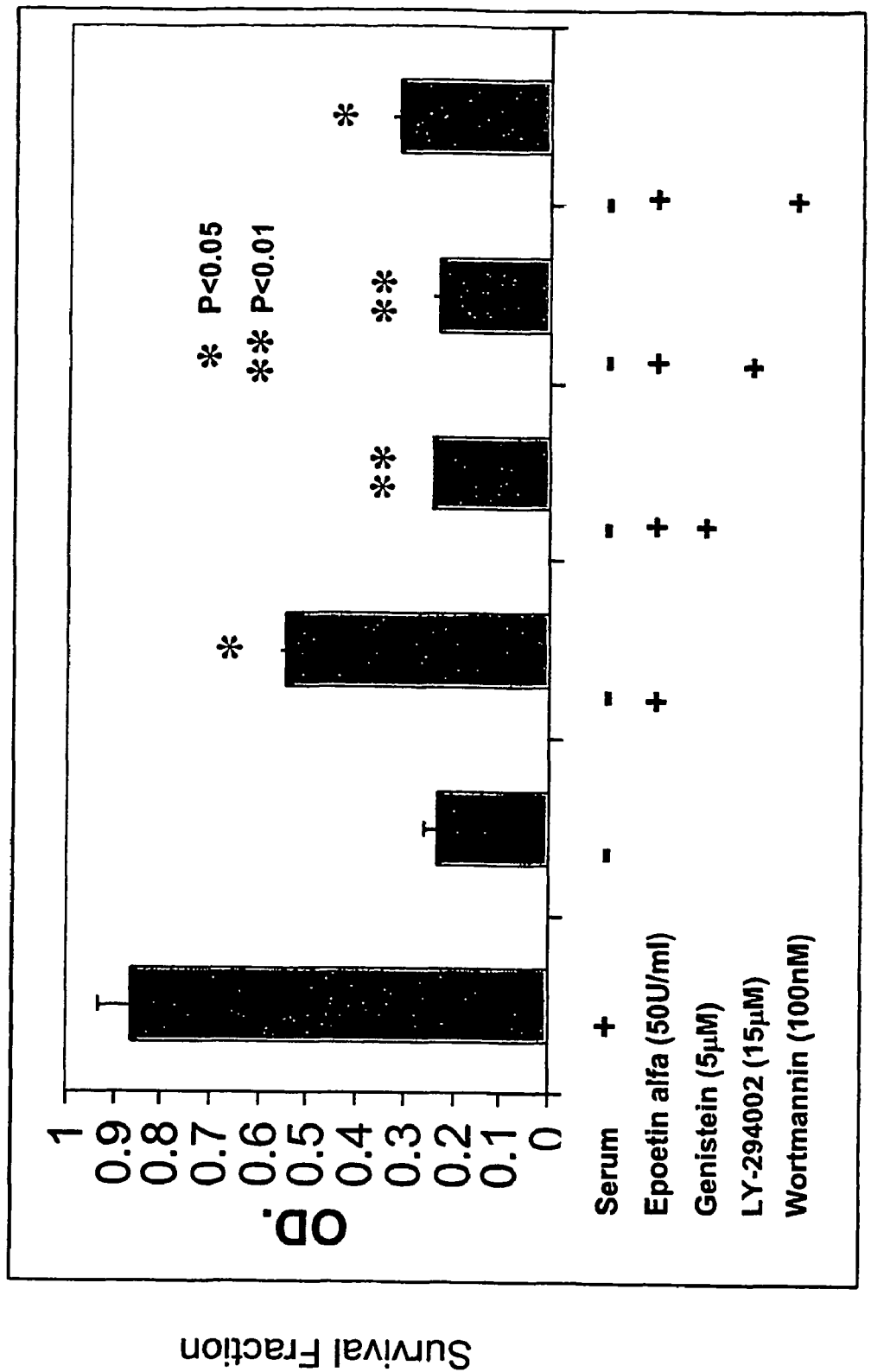
Figure 13 - Erythropoietin Protects Gliomas Against Serum Withdrawal

SEQUENCE LISTING

<160> NUMBER OF SEQ ID NOS: 1

<210> SEQ ID NO 1
<211> LENGTH: 18
<212> TYPE: DNA
<213> ORGANISM: Artificial
<220> FEATURE:
<223> OTHER INFORMATION: Oligonucleotide probe from the erythropoietin
      enhancer region contained HIF-1 binding site

<400> SEQUENCE: 1
gccctacgtg ctgtctca                                               18

ERYTHROPOIETIN AND ERYTHROPOIETIN RECEPTOR EXPRESSION IN HUMAN CANCER

RELATED APPLICATION

This application claims the benefit of U.S. Provisional Application No. 60/253,941, filed on Nov. 30, 2000, which is herein incorporated by reference in its entirety.

GOVERNMENT SUPPORT

This work was supported by a grant from the National Institute of Health (R01-NS37817).

FIELD OF THE INVENTION

The invention relates generally to the changes in gene expression in malignant tissue compared to normal human tissue. The invention relates specifically to the human Erythropoietin (Epo) and Erythropoietin Receptor (EpoR) expression in malignant cancer tissue.

BACKGROUND OF THE INVENTION

Enhanced red blood cell production mediated by the hormone erythropoietin (Epo) is a well-known adaptive response of humans to hypoxia (Bunn & Poyton (1996) Physiological Rev. 76, 839-845). Normally produced by the adult kidney and the fetal liver, Epo stimulates the development of Epo receptor (EpoR) expressing red blood cell precursors in the bone marrow.

Epo is a glycoprotein (46 kDa) hormone produced by renal interstitial cells within the kidney that regulate the production of red blood cells in the marrow. These cells are sensitive to low arterial oxygen concentration and will release erythropoietin when oxygen is low (hypoxia). Erythropoietin stimulates the bone marrow to produce more red blood cells thereby increasing the oxygen carrying capacity of the blood. Epo exerts its effect by binding to EpoR on the surface of erythrocyte precursors in the bone marrow. Epo expression, however, has been observed on cells from other normal tissues in addition to renal interstitial cells including enterocytes, trophoblast and neuronal cells. The protein sequence for Epo, 193 amino acids in length, can be found in GenBank under Accession No. 1104303A (Jacobs et al. (1995) Nature 313, 806-810), which is incorporated herein by reference in its entirety.

The protein sequence for the erythropoietin receptor, 508 amino acids in length, can be found in GenBank, under Accession No. AAA52403 (Jones et al. (1990) Blood 76, 31-35), which is also incorporated herein by reference in its entirety.

The measurement of Epo in the bloodstream can indicate bone marrow disorders or kidney disease. Normal levels of erythropoietin are 0 to 19 mU/ml (milliunits per milliliter). Elevated levels can be seen in polycythemia rubra vera, a condition characterized by enlargement of the spleen and the increased production of red blood cells by bone marrow. Lower than normal values are seen in chronic renal failure leading to anemia. Chronic renal failure leads to anemia, in part, because of the progressive absence of adequate Epo production for the maintenance of erythropoiesis.

Hypoxia is a predominant feature of solid tumors, which comprise approximately ninety percent of all human cancers. Adaptive responses to hypoxia in solid tumors has been correlated with enhanced aggressiveness, reduced tumor cell death and diminished tumor response to both radiation and chemotherapy. Epo expression has been observed in different hematopoietic and non-hematopoietic malignancies and has been shown to mediate autonomous growth of erythrocytic leukemia cells expressing EpoR.

Epo and EpoR expression has recently been demonstrated in several other normal tissues in addition to the kidney (Marti et al. (1996) Eur. J. Neurosci. 8, 666-676; Kling et al. (1998) Pediatr. Res. 43, 216-221; Juul et al. (1999) Pediatr. Dev. Pathol. 2, 148-158; Juul et al. (1999) Pediatr. Res. 46, 263-268; Benyo & Conrad (1999) Biol. Reproduct. 60, 861-870) suggesting a wider biological role for Epo signaling. Ectopic Epo expression also has been observed in several different haematopoietic and non-haematopoietic malignancies (Mitjavila et al. (1991) J. Clin. Invest. 88, 789-797; Tachibana et al. (1991) Neurosurg. 28, 24-26) and can, in fact, mediate autonomous growth of EpoR expressing erythrocytic leukemia cells (Mitjavila et al. (1991) J. Clin. Invest. 88, 789-797). Other studies examining the effects of recombinant erythropoietin on cell lines derived from a wide range of tumors including two breast cancer cell lines determined that no significant stimulation of cancer cell proliferation occurred in response to Epo, in particular low doses of erythropoietin.

In solid neoplasias, adaptive responses to hypoxia are correlated with enhanced aggressiveness (Schmaltz et al. (1998) Mol. Cell. Biol. 18, 2845-2854), poor responses to chemo- and radiation-therapy (Kalra et al. (1993) Int. J. Cancer 54, 650-655; Brown (1999) Cancer Res. 59, 5863-5870), and reduced apoptosis (Graeber et al. (1996) Nature 379, 88-91). Many common human cancers over-express the hypoxia-inducible transcription factor HIF-1, which regulates the expression of Epo as well as several genes required for enhancing hypoxic survival of cancer cells including genes coding for glycolytic enzymes, glucose transporters, and vascular endothelial growth factor (Semenza (1999) Ann. Rev. Cell. Dev. Biol. 15, 551-578). The role of Epo and EpoR in the mechanisms by which hypoxic cancer cells gain a growth advantage and escape cell death has not been previously elucidated.

Tumor hypoxia is recognized as a major factor in tumor resistance to chemotherapy and radiation therapy although the underlying mechanisms are unknown. Hypoxia induces adaptive responses in cells largely by activating the expression of several genes under the regulation of hypoxia-inducible factor-1 (HIF-1), a heterodimeric transcription factor composed of HIF-1α and HIF-1β subunits. The HIF-1α subunit is unique to HIF-1 while HIF-1β can dimerize with several different transcription factors. A decrease in cellular oxygen concentration increases HIF-1α protein levels, which in turn determines the level of HIF-1 activity. Hypoxic regions of gliomas have been shown to highly express HIF-1α (Zagzag et al. (2000) Cancer 88, 2606-2618) as well as several HIF-1 regulated genes including vascular endothelial growth factor and glucose transporters.

Epo is among the most-studied HIF-1-regulated genes. This glycoprotein hormone, normally produced by the kidney and fetal liver, acts via EpoR to stimulate growth, prevent apoptosis, and induce differentiation of red blood cell precursors. Epo and EpoR are also expressed in the nervous system during development and in adult brain following ischemic injury (Sasaki et al. (2001) News Physiol. Sci. 16, 110-113). Several in vitro and in vivo studies have demonstrated a potent neuroprotective effect of erythropoietin in cerebral ischemia, which appears to be mediated by an inhibition of apoptosis (Cerami (2001) Semin. Hematol. 38, 33-39; Digicaylioglu et al. (2001) Nature 412, 641-647). EpoR activation stimulates tyrosine phosphorylation of several proteins, which impact upon multiple signaling pathways capable of promoting cell survival (Cheung et al. (2001) Nephron 87, 215-222). These include the activation of Jak-2, STAT-5, and the PI3K pathway.

Recombinant Epo is now being used therapeutically in cancer patients. Specifically, Epo is used to treat anemia in cancer patients undergoing chemotherapy. Chemotherapy-induced anemia is mainly due to the renal impairment induced by anti-neoplastic drugs which leads to insufficient renal production of Epo with a consequent reduction in red blood cell production. Epo therapy has therefore been widely used as a substitute for blood transfusions in patients undergoing chemotherapy, particularly in breast cancer patients. Accordingly, the role of Epo in the development and progression of certain solid tumors needs to be elucidated.

SUMMARY OF THE INVENTION

The present invention relates to the elucidation of the role of Epo in the development and progression of certain solid tumors, including those found in breast, cervical, uterine, ovarian, prostate and brain cancer.

In one embodiment, the invention relates to a method of detecting a solid tumor in a patient comprising measuring erythropoietin or erythropoietin receptor expression in a patient sample wherein the level of expression is indicative of the presence of a tumor. In a preferred embodiment both erythropoietin and erythropoietin receptor expression are measured in the patient sample.

The invention also encompasses a method of evaluating the progression of a solid tumor in a patient comprising measuring the level erythropoietin or erythropoietin receptor expression in a patient sample, wherein an alteration in the level of expression is indicative of a change in the progression of the tumor. In one embodiment of this method, a decrease in the level of expression is indicative of a decrease in tumor progression. In another embodiment, an increase in the level of expression is indicative of an acceleration in tumor progression.

In one embodiment, the expression is determined by measuring the level of erythropoietin or the erythropoietin receptor polypeptide. In an alternative embodiment, the expression is determined by measuring the level of a nucleic acid encoding erythropoietin or the erythropoietin receptor. In a preferred embodiment, the nucleic acid is amplified using polymerase chain reaction. Furthermore, the nucleic acid can be mRNA and the mRNA can be reversed transcribed into DNA before amplification.

In the methods of the present invention, the patient sample is isolated from any tissue in which normal cells are negative for the presence of erythropoietin and the erythropoietin receptor or in cells in which a baseline level of expression is ascertained. In a preferred embodiment, the patient sample can be isolated from mammary gland, cervix, uterus, lymph node, blood and cerebrospinal fluid. The methods of the invention can be used to detect, diagnose and treat tumors including, but not limited to, breast, cervical, uterine, ovarian, prostate and brain cancer.

In yet another embodiment, the invention includes a method of inhibiting erythropoietin-dependent cell proliferation of a solid tumor in a patient comprising the step of administering an effective amount of an antagonist of the erythropoietin receptor. In one embodiment, the antagonist is an antibody against the erythropoietin receptor. In a related embodiment, the invention includes a method of inhibiting erythropoietin-dependent cell proliferation of a solid tumor in a patient comprising the step of administering an effective amount of an antagonist of erythropoietin. In a preferred embodiment, the antagonist is an antibody against erythropoietin. In a more preferred embodiment the antibody prevents or inhibits the binding of erythropoietin to the erythropoietin receptor. In a most preferred embodiment, the antibody is monoclonal and is humanized.

In a further embodiment, a cytotoxic drug is in combination with the antagonist. In this embodiment, the invention can be used to treat tumors from cancers including breast, cervical, uterine, ovarian, prostate and brain cancer. In the case of breast cancer, the antagonist can be administered locally through a individual breast duct. In yet a further embodiment, the methods can further comprise the step of administering red blood cell transfusions.

In a related embodiment, the invention includes a method of inhibiting erythropoietin-dependent cell proliferation of a solid tumor in a patient comprising the step of administering an effective amount of an antagonist of erythropoietin in combination with an effective amount of an antagonist of the erythropoietin receptor. In one embodiment, the antagonist can be either a peptide or an antibody.

In a final embodiment, the invention includes a method for assessing the effects of erythropoietin administration for treatment of anemia in a cancer patient following chemotherapy comprising measuring the level of erythropoietin receptor expression in a patient sample wherein increased expression is a negative indicator for the administration of erythropoietin.

BRIEF DESCRIPTION OF FIGURES

This patent application contains at least one drawing executed in color. Copies of the patent publication with color drawings will be provided by the Patent and Trademark Office upon request and payment of the necessary fee.

FIG. 1—Human breast carcinoma cell lines display hypoxia-enhanced Epo and EpoR expression. (a) RT-PCR demonstrating basal expression of Epo as well as EpoR mRNA in MCF-7 cells and BT-549 cells. Epo mRNA expression was markedly stimulated following hypoxic treatment with 1% oxygen for four hours while EpoR mRNA was stimulated to a much lesser extent. (b,c) EpoR protein expression in human breast cancer cell lines. In both the MCF-7 and BT-549 cell lines a strongly immunoreactive band at ~66 kiloDaltons was identified with the anti-EpoR antibody (arrows). Staining of this band was specifically abolished when antibody was pre-incubated with EpoR peptide against which the antiserum was raised (+). Exposure of MCF-7 cells to hypoxia for twenty-four hours markedly enhanced EpoR protein expression (c). Two independent controls and hypoxic samples are represented in this figure. Less MCF-7 protein was loaded in (c) than in (b). (d) Immunocytochemical analysis of basal Epo and EpoR protein expression of MCF-7 cultures was localized to a fraction of the cells while exposure to hypoxia for twenty-four hours induced prominent staining of nearly all cells. Similar results were seen with BT-549 cells (not shown) (N=normoxia=21% oxygen; H=hypoxia=1% oxygen; Scale bar=10 mm).

FIG. 10—EpoR expression in human glioma cells is enhanced by hypoxia. (a) Three human malignant glioblastoma cells lines U87, U251, U373 and normal human astrocytes (NHA) were assayed for EpoR expression by western blotting. EpoR (approximately 66 kDa) was prominently expressed by all three glioma cell lines but only faintly in normal human astrocytes. (b) Hypoxia sensitivity of EpoR expression was tested in U251 cells. When subjected to six-hour treatments of either hypoxia (1% oxygen) or 150 µM desferrioximine (DFX) these cells responded by dramatically upregulating the level of HIF-1α protein and HF-1 gelshift activity. RT-PCR analysis for mRNA expression showed a prominent induction of Epo by both hypoxia and DFX. EpoR mRNA was expressed basally, was less prominently induced by hypoxia, and was not induced by DFX. Immunoreactive EpoR protein levels were however enhanced by both hypoxia and DFX. Experiments are representative of three repeats.

FIG. 11—Epo can activate signaling pathways in human gliomas. 10 U/ml rhEpo were added to U251 cells in serum free media. (a) rhEpo induced a prominent activation of tyrosine phosphorylation in several proteins as assessed by western blotting. Tyrosine phosphorylation by a single dose of Epo was activated within one minute and lasted for more than two hours. (b) Tyrosine phosphorylation could also be elicited by an Epo-mimetic peptide (EMP) and by Epoetin-alfa, the clinically used form of Epo (thirty minute treatments). (c) rhEpo also stimulated Jak-2 and STAT-5 tyrosine phosphorylation, as well as phosphorylation of the PI3K substrate Akt. These data establish that EpoR associated signaling pathways can be activated by Epo in human gliomas.

FIG. 12—Epo protects glioma cells from Cisplatin toxicity. The effect of epoetin-alfa on toxicity of cisplatin in U251 cells was examined. Overnight treatment of U251 cells in serum-free media with 10 mM Cisplatin killed approximately 80% of cells (survival fraction=0.2). Epoetin-alfa was able to dose-dependently reverse cisplatin toxicity. Similar results were seen with BCNU and Taxol (data not shown). These results demonstrate that Epo signaling can contribute to chemotherapy resistance in human glioma cells. ($*p<0.05$ and $**p<0.01$ versus Cisplatin alone).

FIG. 13—EPO can protect glioma cells from serum withdrawal. U251 cells were cultured in serum-free media. Approximately 80% cell death was observed forty-eight hours after serum withdrawal, which could be reduced by Epoetin-alfa ($*p<0.05$ versus serum-fed cells). The protective effect of Epoetin-alfa was blocked by inhibitors of tyrosine kinases (Genistein) or PI3 kinase (LY294002 and Wortmannin) ($*p<0.05$ and $**p<0.01$ versus Epoetin-alfa alone). These data further demonstrate that Epo signaling in glioma cells serves to activate cell survival signaling pathways.

DETAILED DESCRIPTION

I. General Description

Figure 2:
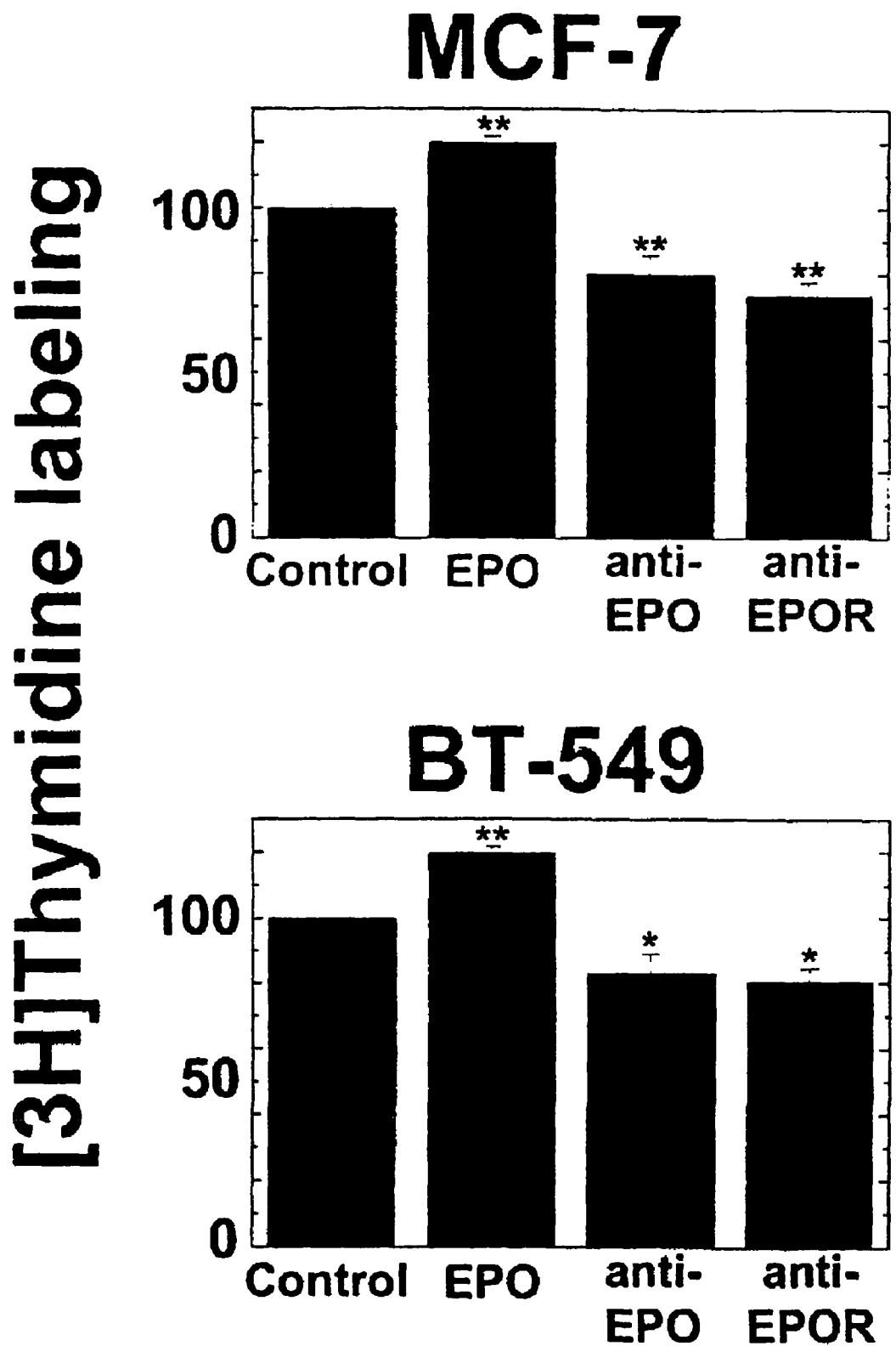
FIG. 2—Erythropoietin receptor activation stimulates DNA synthesis in breast cancer cells. $^3$H-thymidine incorporation into both MCF-7 and BT-549 cell lines was enhanced by addition of exogenous rhEpo (100 units/ml) to the culture medium and was inhibited by the addition of 2 mg/ml of either anti-Epo or anti-EpoR antiserum. (**p<0.01, *p<0.05, Student's two-tailed T-test)

The invention is derived from the discovery that Epo as well as EpoR are induced by hypoxia in human malignant tumor cells, especially breast and cervical carcinoma. The invention relates to the modulation of Epo-dependent proliferation of malignant cells, preferably blockade of Epo signaling at EpoR, thereby inhibiting the proliferation of malignant tumor cells.

II. Specific Embodiments

A. Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some preferred methods and materials are described.

As used herein, the term "binding" refers to the adherence of molecules to one another, such as, but not limited to, enzymes to substrates, antibodies to antigens, and DNA or RNA strands to their complementary strands. Binding occurs because the shape and chemical nature of parts of the molecule surfaces are complementary. A common metaphor is the "lock-and-key" used to describe how enzymes interact with their substrate.

As used herein, the term "detection agent" refers to any composition used to detect Epo or EpoR expression. Examples include, but are not limited to, antibodies which bind to Epo or EpoR and nucleic acid probes and primers which hybridize to DNA or RNA encoding Epo or EpoR.

As used herein, the term "patient sample" refers to any tissue or bodily fluid isolated from a mammal. Tissue patient samples include, but are not limited to, lymph node aspirate, lymph node biopsy, spleen tissue, fine needle aspirate, skin biopsy or organ tissue biopsy. Bodily fluid patient samples include, but are not limited to, samples where the body fluid is blood, serum, lymph fluid, ascites, serous fluid, pleural effusion, sputum, cerebrospinal fluid, lacrimal fluid, stool or urine.

As used herein, the term "malignant cell" refers to any cell having anaplastic properties, capable of invasion into tissue where it is not normally found, or capable of facilitating metastasis of a tumor. These cells are characterized by uncontrolled growth and will invade surrounding tissues and spread to distant sites of the body thus mediating metastasis. The term "malignant" as used herein is synonymous with the term "cancer" and any form thereof.

As used herein, the term "therapeutic agent" refers to any composition which inhibits the activity of Epo and EpoR. Examples include, but are not limited to, antibodies to Epo or EpoR, small molecules which bind to EpoR, nucleic acid probes and primers which hybridize to DNA or RNA encoding Epo or EpoR and antisense DNA or RNA which binds to complementary DNA or RNA encoding Epo or EpoR.

B. Detection Methods

One aspect of the present invention relates to a method of detecting malignant cells or portions thereof from a solid tumor in a patient sample. This method involves providing a detection agent, such as an antibody or binding portion thereof, probe or ligand, which binds to EpoR expressed on such malignant cells. The detection agent is preferably bound to a label effective to permit detection of the cells or portions (e.g., EpoR or fragments thereof liberated from malignant cells) thereof upon binding of the agent to the cells. The patient sample is contacted with the detection agent having a label under conditions effective to permit binding of the agent to EpoR expressed on any of the cells or portions thereof in the patient sample. The presence of any malignant cells or portions thereof in the patient sample is established by detection of the label.

In a preferred embodiment, EpoR protein levels are assayed to detect malignant cells in a patient sample as the level of induction of EpoR protein expression may be more easily detected than mRNA induction. In its preferred form, contacting involves combining the agent with a tissue sample isolated from the mammal under conditions effective to permit binding of the agent to EpoR expressed on any of the malignant cells or portions thereof in the patient sample. In one aspect of the preferred form, the agent can bind to the extracellular or intracellular domain of EpoR. Agents which bind to the intracellular domain are indicative of the presence of fragments of cells as this domain may not be accessible in intact cells.

Another embodiment of the invention encompasses a method for accessing the effects of Epo administration for treatment of anemia following chemotherapy by measuring the level of EpoR expression in a patient sample. In its preferred form, detection of increased expression of EpoR is a negative indicator for the administration of erythropoietin for the treatment of anemia following chemotherapy in cancer patients. Such detection avoids the adverse effects associated with stimulation of cell proliferation in malignant tumors by exogenously administered Epo.

Another means for detecting malignant cells or portions thereof in a patient sample employs detection of Epo expression in the patient sample. This method involves providing a detection agent, such as an antibody or binding portion thereof, probe or ligand, which binds to the Epo secreted by such malignant cells. The detection agent is preferably bound to a label effective to permit detection of the malignant cells or portions thereof upon binding of the agent to the cells. The patient sample is contacted with the agent having a label under conditions effective to permit binding of the agent to Epo or portions thereof secreted by any of the malignant cells in the patient sample. The presence of any malignant cells or portions thereof in the patient sample is detected by detection of the label. In its preferred form, contacting involves combining the agent with a patient sample isolated from the mammal under conditions effective to permit binding of the agent to the Epo or portions thereof secreted by any of the malignant cells or portions thereof in the patient sample.

In another embodiment of the invention, Epo protein levels are assayed to detect malignant or benign tumor cells in mammary tissue samples from patients who smoke. This method involves providing a detection agent, such as an antibody or binding portion thereof, probe or ligand, which binds to the Epo secreted by malignant or benign tumor cells, preferably in breast epithelial tissue. The detection agent is preferably bound to a label effective to permit detection of the tumor cells or portions thereof upon binding of the agent to the cells. The patient sample is contacted with the agent having a label under conditions effective to permit binding of the agent to Epo or portions thereof secreted by any of the malignant or benign tumor cells in the patient sample. The presence of any tumor cells or portions thereof in the patient sample is detected by detection of the label. In its preferred form, contacting involves combining the agent with a sample from a patient who is a smoker, the sample isolated from the mammal under conditions effective to permit binding of the agent to the Epo or portions thereof secreted by any of the tumor cells or portions thereof in the patient sample. Elevated levels of Epo, particularly in breast epithelial tissue, from smokers are indicative of either malignant or benign tumors.

In yet another means for detecting EpoR expression on, or Epo secretion by malignant cells, the instant invention comprises a method for identification of malignant cells in a patient sample by amplifying and detecting nucleic acids corresponding to, or encoding EpoR or Epo. The patient sample can be any tissue or fluid in which malignant cells might be present wherein EpoR and Epo are not normally expressed. Preferred embodiments include lymph node aspirate, lymph node biopsy, spleen tissue, fine needle aspirate, skin biopsy or organ tissue biopsy. Other embodiments include samples where the body fluid is blood, serum, lymph fluid, ascites, serous fluid, pleural effusion, sputum, cerebrospinal fluid, lacrimal fluid, stool or urine. In patient samples where Epo or EpoR are normally expressed, a baseline level of expression may be determined and changes in the level of expression detected.

Nucleic acids used as templates for amplification are isolated from cells contained in the patient sample according to standard methodologies (Sambrook et al. (1989) Molecular Cloning—A Laboratory Manual, Cold Spring Harbor Laboratory Press). The nucleic acid may be genomic DNA or fractionated or whole cell RNA. Where RNA is used, it may be desired to convert the RNA to a complementary cDNA. In a preferred embodiment, the RNA is whole cell RNA and is used directly as the template for amplification. Pairs of primers that selectively hybridize to genes corresponding to specific markers are contacted with the isolated nucleic acid under conditions that permit selective hybridization. Once hybridized, the nucleic acid primer complex is contacted with one or more enzymes that facilitate template-dependent nucleic acid synthesis.

Multiple rounds of amplification are conducted until a sufficient amount of amplification product is produced. Next, the amplification product is detected. In certain applications, the detection may be performed by visual means including detection in situ (i.e., in situ immunohistochemistry or in situ hybridization). Alternatively, the detection may involve indirect identification of the product via chemiluminescence, radioactive scintigraphy of incorporated radioactive label or fluorescent label.

Additional assay formats may be used in the methods for detecting expression of a nucleic acid encoding Epo or EpoR by malignant cells. For instance, mRNA expression may be monitored directly by hybridization to the nucleic acids encoding Epo or EpoR. In these assays, total RNA or mRNA is isolated from the patient sample by standard procedures such those disclosed in Sambrook et al. (1989) Molecular Cloning—A Laboratory Manual, Cold Spring Harbor Laboratory Press.

Probes to detect differences in RNA expression levels between malignant cells and control cells which do not express Epo or EpoR may be prepared from sequences encoding Epo or EpoR. It is preferable, but not necessary, to design probes which hybridize only with target nucleic acids under conditions of high stringency. Only highly complementary nucleic acid hybrids form under conditions of high stringency. Accordingly, the stringency of the assay conditions determines the amount of complementarity which should exist between two nucleic acid strands in order to form a hybrid. Stringency should be chosen to maximize the difference in stability between the probe:target hybrid and potential probe:non-target hybrids.

Probes may be designed from the nucleic acids encoding EpoR and Epo through methods known in the art. For instance, the G+C content of the probe and the probe length can affect probe binding to its target sequence. Methods to optimize probe specificity are commonly available in Sambrook et al. (1989) Molecular Cloning—A Laboratory Manual (Cold Spring Harbor Laboratory Press) or Ausubel et al. (1995) Current Protocols in Molecular Biology (Greene Publishing).

Hybridization conditions are modified using known methods, such as those described by Sambrook et al. (1989) and Ausubel et al. (1995) as required for each probe. Hybridization of total cellular RNA or RNA enriched for polyA+RNA can be accomplished in any available format. For instance, total cellular RNA or RNA enriched for polyA+RNA can be affixed to a solid support and the solid support exposed to at least one probe comprising at least one, or part of one of the sequences of the invention under conditions in which the probe will specifically hybridize. Alternatively, nucleic acid fragments comprising at least one, or part of one of the sequences of the invention can be affixed to a solid support, such as a silicon based wafer or a porous glass wafer. The wafer can then be exposed to total cellular RNA or polyA+ RNA from a sample under conditions in which the affixed sequences will specifically hybridize. Such wafers and hybridization methods are widely available, for example, those disclosed by Beattie (1995) WO 95/11755. By examining for the ability of a given probe to specifically hybridize to an RNA sample from a normal, non-malignant patient sample and from a sample to be tested, patient samples containing malignant cells are identified.

Hybridization for qualitative and quantitative analysis of mRNA may also be carried out by using a RNase Protection Assay (i.e., RPA, see Ma et al. Methods (1996) 10, 273-238). Briefly, an expression vehicle comprising cDNA encoding the gene product and a phage specific DNA dependent RNA polymerase promoter (e.g., T7, T3 or SP6 RNA polymerase) is linearized at the 3' end of the cDNA molecule, downstream from the phage promoter, wherein such a linearized molecule is subsequently used as a template for synthesis of a labeled antisense transcript of the cDNA by in vitro transcription. The labeled transcript is then hybridized to a mixture of isolated RNA (i.e., total or fractionated mRNA) by incubation at 45° C. overnight in a buffer comprising 80% formamide, 40 mM Pipes (pH 6.4), 0.4 M NaCl and 1 mM EDTA. The resulting hybrids are then digested in a buffer comprising 0.040 mg/ml ribonuclease A and 0.002 mg/ml ribonuclease. After deactivation and extraction of extraneous proteins, the samples are loaded onto urea/polyacrylamide gels for analysis.

The methods of the present invention can be used to screen patients for diseases associated with the presence of malignant cells or portions thereof, in particular, malignancies of solid tumors whose growth is affected by or dependent on Epo. Such malignancies or solid tumors include breast, cervical, uterine, ovarian, prostate and brain cancer. Alternatively, it can be used to identify the recurrence of such diseases, particularly when the disease is localized in a particular biological material of the patient. For example, recurrence of malignant breast cancer in a female patient may be encountered following radical mastectomy. Using the method of the present invention, this recurrence can be detected by monitoring for the presence of Epo or EpoR expression as described above in a series of patient samples from the patient. In another example, the presence of cervical cancer can be monitored by measuring Epo or EpoR expression in a pap smear isolated from the female patient.

C. Patient Samples

The methods of the present invention find use in diagnosis, employing tissue cytology or lysates of tissue in detecting EpoR or Epo. A wide variety of techniques and protocols exist for detecting an antigen in a sample suspected of containing the antigen. For instance, the presence of EpoR or Epo can be determined immunologically by applying conventional immunoassays or histochemical staining techniques using antibodies reactive with the proteins expressed on the cell surface and secreted into the blood. Protocols involve a wide variety of labels, which labels include radio-nucleotides, enzymes, fluorescers, fluorescer-quencher combinations, chemiluminescers, magnetic particles, radiopaque dyes, and the like. These labels can be directly conjugated to the monoclonal antibody through a variety of covalently bonded linking groups and functionalities. Some of the techniques involve having one of the members of the antigen-antibody complex bound to a support, such as a particle or vessel wall, while other of the assays are performed in solution without a separation step. In a number of assays, the antibody need not be labeled, such as in a hemagglutination assay, or where anti-immunoglobulin is employed and the anti-immunoglobulin is labeled, so as to provide for indirect labeling of the subject monoclonal antibody. Assays which can be employed include assays such as enzyme-linked immunosorbent assay (Harris & Winkelmann (1996) Am. J. Hematol. 52, 8-13), radio-immunoassay, fluorescence immunoassay (Frye et al. (1987) Oncogene 4, 1153-1157) and the like.

Often, a sample is pretreated in some manner prior to performing a screening assay, generally immunoassay. A wide variety of immunological assay methods are available for determining the formation of specific antibody antigen complexes. Numerous competitive and non-competitive protein binding assays have been described in the scientific and patent literature and a large number of such assays are commercially available. It is well within the skill of one skilled in the art to perform such screening. Sample preparation will vary depending on the source of the patient sample. Cell or tumors and other tissue samples may be prepared by lysing the cells. Serum samples typically can be prepared by clotting whole blood and isolating the supernatant in accordance with well known methods.

For diagnosis of a malignant tumor, biopsy specimens are the most likely source of samples for analysis. Conventional immunohistochemical staining techniques can be used for detecting EpoR or Epo in tissue samples. For example, the tissue sample may be fixed in formalin or other standard histological preservatives, dehydrated and embedded in paraffin as is routine in any hospital pathology laboratory. When paraffin embedded preparations are used, the antigen should be evaluated to determine whether the preparation denatures the antigen for analysis. Sections are cut from the paraffin embedded material and mounted on glass slides or the sections are prepared from cryo-preserved tissue. Alternatively, cytological preparations can be used. For example, cells from the tissue sample can be fixed on a slide, typically by exposure to formalin in a buffer at physiologic pH, followed by suspension in acetone and pelleting onto gelatin-coated slides by centrifugation. The cellular antigen can be localized, either by exposure to labeled antibody or by exposure to unlabeled antibody and a labeled secondary antibody. The amount of the cell surface protein or antigen in the sample is directly proportional to the amount of bound label.

Biological fluids such as semen, serum, urine, saliva and sweat also may be assayed for the presence of EpoR or Epo as a way of monitoring for the presence or recurrence of a malignant tumor, particularly breast, cervical, uterine, ovarian, prostate and brain cancer. In one embodiment, the contacting step can be carried out in a sample of serum or urine or other body fluid, such as to detect the presence of Epo or EpoR in the body fluid. When the contacting is carried out in a serum or urine sample, it is preferred that the agent recognize substantially no antigens circulating in the blood other than Epo or EpoR. Since Epo is normally found in the blood, the presence of tumor will be detected by any significant increase in the level of expression of Epo in serum, urine, or other body fluid. It may therefore be necessary to establish a normal baseline level for Epo or EpoR expression for each patient which can be compared to levels following treatment of the malignant tumor. Preferred baseline levels for Epo protein expression in human serum are about 0 to about 19 mU/ml. Preferred Epo baseline levels in saliva are generally about fifteen to thirty percent of serum values. Preferred Epo baseline levels in cerebral spinal fluid range from about 0.98 to 3.20 mU/ml in adults to about 4.0 to 5.0 mU/ml in children.

Thus, the agents and methods of the present invention can be used to determine the effectiveness of a cancer treatment protocol by monitoring the level of Epo or EpoR in serum, urine or other body fluid. In one example, levels of Epo or EpoR expression can be measured in the sputum from a patient to detect lung cancer. In a related example, Epo or EpoR expression can be measured in the fluid extracted from the lungs of a patient undergoing bronchiolar lavage to detect lung cancer. In yet another example, Epo or EpoR expression can be measured in the cerebral spinal fluid of a patient to detect brain cancer. In particular, elevated levels of Epo or EpoR expression can be used to detect glioma, medulloblastoma and astrocytoma, including glioblastoma.

In another embodiment of the method of detecting malignant cells in accordance with the present invention, the detection agent, such as the antibody or binding portion thereof, peptide, probe or ligand, binds to and is internalized with EpoR of such cells. Again, the agent is bound to a label effective to permit detection of the cells or portions thereof upon binding of the agent to and internalization of the agent with EpoR.

D. Treatment of Malignant Tumors

One aspect of the present invention relates to the treatment of malignant tumors through inhibition of Epo- and EpoR-dependent cell proliferation. In one embodiment, the invention relates to a method of inhibiting the growth or metastatic potential of malignant cells in a solid tumor by inhibiting Epo and/or EpoR. Alternatively, the method can be used to kill or ablate malignant cells in a solid tumor. The process involves providing a therapeutic agent, such as an antibody or binding portion thereof, probe, peptide or small molecule ligand, which binds to EpoR expressed on such cells. The therapeutic agent can be used alone or can be bound to a substance effective to kill the cells upon binding of the agent to the cells. These agents are then contacted with the cells under conditions effective to permit binding of the agent to the extracellular domain of EpoR. Binding to EpoR results in inhibition of cell proliferation when the therapeutic agent is used alone or in the death of the malignant cells when used in combination with a cytotoxic agent. In its preferred form, such contacting is carried out in a living mammal by administering the agent to the mammal under conditions effective to permit both binding of the agent to the extracellular domain of EpoR and killing of the malignant cells or inhibiting their proliferation.

In one embodiment the invention includes a method of inhibiting Epo-dependent cancer cell proliferation in a solid tumor in a patient by administering an effective amount of an antagonist of EpoR to block the binding of Epo at EpoR. The invention also includes a method of inhibiting Epo-dependent cancer cell proliferation in a solid tumor in a patient by administering an effective amount of an antagonist of Epo to prevent its binding to EpoR. In a preferred embodiment, the method comprises blockade of the EpoR on endothelial cells as a means to block angiogenesis of the tumor. Thus, the therapeutic agents can be antagonist of either Epo or EpoR and can be administered individually or in combination. Preferred antagonists include, antibodies against either Epo or EpoR, peptides and small molecule antagonists which bind to EpoR.

In one embodiment of the method of ablating or killing malignant cells in accordance with the present invention, the therapeutic agent binds to and is internalized with EpoR expressed on such cells. The agent can be bound to a substance effective to kill the cells upon binding of the agent to EpoR and upon internalization of the agent with EpoR. The mechanism by which the agent is internalized with EpoR is not critical to the practice of the present invention. For example, the agent can induce internalization of EpoR. Alternatively, internalization of the agent can be the result of routine internalization of EpoR.

When the agents are used for treatment or therapy, effective amounts can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat and bronchial tubes. In one embodiment, the agents may be administered locally through an individual breast duct where the malignant cells are localized. The effective dosage administered will be dependent upon the age, health and weight of the recipient, kind of concurrent treatment, if any, frequency of treatment and the nature of the effect desired. While individual needs vary, determination of optimal ranges of effective amounts of each component is within the skill of the art. Typical dosages comprise 0.0001 to 0.100 mg/kg body weight. The preferred dosages comprise 0.0001 to 0.10 mg/kg body weight. The most preferred dosages comprise 0.0001 to 0.001 mg/kg body weight.

They may be administered alone or with pharmaceutically or physiologically acceptable carriers, excipients, or stabilizers, and can be in solid or liquid form such as, tablets, capsules, powders, solutions, suspensions, or emulsions.

The solid unit dosage forms can be of the conventional type. The solid form can be a capsule, such as an ordinary gelatin type containing the agent, such as an antibody or binding portion thereof, of the present invention and a carrier, for example, lubricants and inert fillers such as lactose, sucrose or cornstarch. In another embodiment, these compounds are tableted with conventional tablet bases such as lactose, sucrose or cornstarch in combination with binders like acacia, cornstarch or gelatin, disintegrating agents such as cornstarch, potato starch or alginic acid, and a lubricant like stearic acid or magnesium stearate.

The therapeutic agents of the present invention may also be administered in injectable dosages by solution or suspension of these materials in a physiologically acceptable diluent with a pharmaceutical carrier. Such carriers include sterile liquids such as water, liposomes and oils, with or without the addition of a surfactant and other pharmaceutically and physiologically acceptable carrier, including adjuvants, excipients or stabilizers. Illustrative oils are those of petroleum, animal, vegetable or synthetic origin, for example, peanut oil, soybean oil or mineral oil. In general, water, saline, aqueous dextrose and related sugar solution and glycols such as, propylene glycol or polyethylene glycol are preferred liquid carriers, particularly for injectable solutions.

For use as aerosols, the agents of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

The therapeutic agents can also be utilized to kill or ablate malignant cells in vivo. This involves using the agents in combination with a cytotoxic drug to which the agents recognizing EpoR on the malignant cells are bound. This can be accomplished by administering the agents bonded to a cytotoxic drug to a mammal requiring such treatment. The agents of the present invention may be used to deliver a variety of cytotoxic drugs including therapeutic drugs, a compound emitting radiation, molecules of plants, fungal, or bacterial origin, biological proteins, and mixtures thereof. The cytotoxic drugs can be intracellularly acting cytotoxic drugs, such as short-range radiation emitters, including, for example, short-range, high-energy α-emitters.

Where the agents are used alone to inhibit the growth, metastatic potential or physiology of malignant cells, such inhibition can be effected by blocking the autocrine effects of Epo secreted by malignant cells on surrounding malignant cells through its interaction at EpoR. Blockade of EpoR being responsible for inhibition of DNA synthesis associated with increased cell proliferation and transformation.

Therapeutic agents of the present invention can be used in conjunction with other therapeutic treatment modalities. Such other treatments include surgery, radiation, cryosurgery, thermotherapy, hormone treatment, chemotherapy, vaccines, and other immunotherapies.

In one embodiment, the agents can be administered concurrently with red blood cell transfusions. Such transfusions may be necessary to counter the effects of EpoR blockade on normal, non-malignant cells such as the regulation of red blood cell in bone marrow. Thus, the effects of decreased production of red blood cells in the bone marrow due to blockade of Epo binding at EpoR could be countered by administration of red blood cells to the patient.

Also encompassed by the present invention includes a method of inhibiting the growth, metastatic potential or physiology of malignant cells which involves using the therapeutic agents for prophylaxis. For example, these materials can be used to prevent or delay development or progression of a malignant tumor. As provided in the Examples, agents that modulate (up- or down-regulate) the expression of Epo or EpoR such as agonists or antagonists of at least one activity of Epo or EpoR may be used to modulate biological and pathologic processes associated with the Epo or EpoR function and activity. Preferably, the process is inhibition of malignant cell proliferation which may be due to increased DNA synthesis following EpoR activation by Epo. In another embodiment, the present invention includes a method of ablating or killing malignant cells which involves using the agents for prophylaxis. Agents that bind to EpoR can be used to target malignant cells for ablation with cytotoxic agents as discussed above.

As used herein, the methods of the present invention can be practiced on any mammal, so long as the mammal is in need of modulation of a malignant pathological process mediated by EpoR or Epo. The term "mammal" is meant an individual belonging to the class Mammalia. The invention is particularly useful in the treatment of human subjects, in particular, human subjects with a malignant tumor. In a preferred embodiment, the human subjects are breast, cervical, uterine, ovarian, prostate and brain cancer patients with a malignant tumor.

E. Detection & Therapeutic Agents

As discussed above, detection agents suitable for practicing the detection methods of the invention include antibodies, such as monoclonal or polyclonal antibodies. In addition, antibody fragments, half-antibodies, hybrid derivatives, probes and other molecular constructs may be utilized. These detection agents, such as antibodies, binding portions thereof, peptides, probes or ligands, bind to extracellular or intracellular domains of EpoR or portions thereof in malignant cells. As a result, the agents used in the methods of the invention bind to all such cells, not only to cells which are fixed or cells whose intracellular antigenic domains are otherwise exposed to the extracellular environment. Consequently, binding of the detection agents is concentrated in areas where there are malignant cells, irrespective of whether these cells are fixed or unfixed, viable or necrotic. Additionally or alternatively, these agents, such as antibodies, binding portions thereof, probes or ligands, bind to and are internalized with EpoR or portions thereof in malignant cells.

The detection agents used in the methods of the present invention can utilize probes or ligands found either in nature or prepared synthetically by recombinant DNA procedures or other biological or molecular procedures. Suitable probes or ligands are molecules which bind to EpoR or Epo. Other suitable probes or ligands are molecules which bind to and are internalized with EpoR. Such probes or ligands can be, for example, proteins, peptides, lectins or nucleic acid probes.

The therapeutic agents suitable for practicing the treatment methods of the invention also include antibodies, such as monoclonal or polyclonal antibodies. In addition, antibody fragments, half-antibodies, hybrid derivatives, peptides, probes, and other molecular constructs may be utilized. These therapeutic agents, such as antibodies, binding portions thereof, probes or ligands, bind to Epo or the extracellular domain of EpoR or portions thereof in malignant cells. Consequently, binding of the therapeutic agent is concentrated in areas where there are malignant cells, irrespective of whether these cells are part of a tumor or are metastatic cells invading other tissues. Additionally or alternatively, these agents, such as antibodies, binding portions thereof, peptides, probes or ligands, bind to and are internalized with EpoR or portions thereof in malignant cells.

The therapeutic agents suitable for practicing the treatment methods of the invention also include peptides, preferably synthetic peptides. Peptides capable of binding the EpoR receptor have been previously described (Livnah et al. (1998) 5, 9993-1004) herein incorporated by reference in its entirety.

The therapeutic agents of the present invention can be provided alone or in combination with other agents that modulate a particular pathological process. For example, an agent of the present invention can be administered in combination with other chemotherapeutic agents. As used herein, two agents are said to be administered in combination when the two agents are administered simultaneously or are administered independently in a fashion such that the agents will act at the same time.

The detection and therapeutic agents used in the methods of the invention may be produced by any acceptable means. For instance, monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler & Milstein (1975) Nature 256, 495 -497 which is hereby incorporated by reference. The production of antibodies to Epo and EpoR has also been previously described (Sytkowski & Fisher (1985) J. Biol. Chem. 14727-14731; Morishita et al. (1996) Blood 88:465-471), both references hereby incorporated by reference.

Mammalian lymphocytes are immunized by in vivo immunization of the animal (e.g., a mouse) with EpoR or Epo polypeptides or fragments thereof. Such immunizations are repeated as necessary at intervals of up to several weeks to obtain a sufficient titer of antibodies. Following the last antigen boost, the animals are sacrificed and spleen cells removed. Fusion with mammalian myeloma cells or other fusion partners capable of replicating indefinitely in cell culture is effected by standard and well-known techniques, for example, by using polyethylene glycol (PEG) or other fusing agents (see Milstein & Kohler (1976) Eur. J. Immunol. 6, 511-519 which is hereby incorporated by reference). This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 0.10 ml per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected ten days after each boost. Polyclonal antibodies are then recovered from the serum by affinity chromatography using the corresponding antigen to capture the antibody. Ultimately, the rabbits are euthanized with pentobarbital. This and other procedures for raising polyclonal antibodies are disclosed in Harlow & Lane (1988) Antibodies—A Laboratory Manual (Cold Spring Harbor Press) which is hereby incorporated by reference.

In addition to utilizing whole antibodies, the methods of the present invention encompass use of binding portions of such antibodies. Such binding portions include Fab fragments, F(ab')$_2$ fragments and Fv fragments. These antibody fragments can be made by conventional procedures, such as proteolytic fragmentation procedures, as described in Goding (1983) Monoclonal Antibodies—Principles and Practice (Academic Press) which is hereby incorporated by reference.

Monospecific and bispecific immunoglobulins may also be produced by recombinant techniques in prokaryotic or eukaryotic host cells. Such chimeric antibodies are encoded by immunoglobulin genes that have been genetically engineered so that the light and heavy chain genes are composed of immunoglobulin gene segments belonging to different species. For example, the variable (V) segments of the genes from a mouse monoclonal antibody may be joined to human constant (C) segments. Such a chimeric antibody is likely to be less antigenic to a human than antibodies with mouse constant regions as well as mouse variable regions.

As used herein, the term chimeric antibody also refers to an antibody that includes an immunoglobulin that has a human-like framework and in which any constant region present has at least about 85-90% and preferably about 95% polypeptide sequence identity to a human immunoglobulin constant region, a so-called "humanized" antibody. Hence, all parts of such a humanized antibody, except possibly the complementarity determining regions (CDR) are substantially identical to corresponding parts of one or more native human immunoglobulin sequences. Where necessary, framework residues may also be replaced with those within or across species especially if certain framework residues are found to affect the structure of the CDR. A chimeric antibody may also contain truncated variable or constant regions.

The term "framework region" as used herein, refers to those portions of immunoglobulin light and heavy chain variable regions that are relatively conserved (i.e., other than the CDR) among different immunoglobulins in a single species. As used herein, a "human-like framework region" is a framework region that in each existing chain comprises at least about 70 or more amino acid residues, typically 75 to 85 or more residues, identical to those in a human immunoglobulin. Human constant region DNA sequences can be isolated in accordance with well known procedures from a variety of human cells, but preferably from immortalized B-cells. The variable regions or CDR for producing chimeric immunoglobulins may be similarly derived from monoclonal antibodies capable of binding to EpoR or Epo and will be produced in any convenient mammalian system, including, mice, rats, rabbits, human cell lines or other vertebrates capable of producing antibodies by well known methods. Variable regions or CDR may be produced synthetically, by standard recombinant methods including polymerase chain reaction (PCR) or through phage-display libraries. For phage display methods, see for example, McCafferty et al. (1990) Nature 348, 552-554; Clackson et al. (1990) Nature 352; 624-628; Marks et al. (1993) Biotechnology 11, 1145-1149. Suitable prokaryotic systems such as bacteria, yeast and phage may be employed.

Without further description, it is believed that one of ordinary skill in the art can, using the preceding description and the following illustrative examples, make and utilize the compounds of the present invention and practice the claimed methods. The following working examples therefore, specifically point out preferred embodiments of the present invention, and are not to be construed as limiting in any way the remainder of the disclosure.

EXAMPLES

Example 1

Epo and EpoR Expression in Human Cancer Cell Lines

To investigate whether solid tumors utilize Epo signaling as a mechanism for hypoxic survival, the expression of Epo and EpoR was assayed in human breast cancer cell lines in culture by RT-PCR, Western blot and immunocytochemical analyses.

For cell culture experiments, all culture media was purchased from Life Technologies. All cell lines were obtained from American Type Culture Collection (ATCC) and cultured according to ATCC directions. Hypoxic treatment of cells was performed in an enclosed chamber (Billups Rothbard) flushed with premixed gas mixture (1% oxygen, 5% carbon dioxide, 94% nitrogen) for the indicated times.

Measurements of Epo and EpoR mRNA expression by RT-PCR were performed as previously described (Assandri et al. (1999) J. Physiol. 516, 343-352). RNA was isolated using the Qiagen RNA isolation kit and the two-step GeneAmp RT-PCR kit (PE Biosystems) was used for RT-PCR. Approximately 2 mg/ml RNA and 10 pmol of both the forward and reverse primers were used for each sample. The PCR cycle protocol for the Epo and EpoR primers is 35 cycles at 94° C. for one minute, 56° C. for one minute and 72° C. for two minutes. The RT-PCR products were then run on a 2% agarose gel. DNA standard used was the 100 base pair DNA Ladder from FMC Bioproducts. The 449 base pair RT-PCR product was purified with a PCR purification kit (Qiagen) and sequenced using ABI Prism automated sequence analyzer.

For Western blot experiments, cell lysates were normalized for protein, subjected to SDS-PAGE, transferred to nitrocellulose and stained with affinity purified, polyclonal anti-EpoR antibody (1:1000 dilution) (Santa Cruz Biotechnology) in the presence and absence of blocking peptide (5:1 peptide: antibody ratio). A goat anti-rabbit secondary antibody conjugated with horseradish peroxidase (Amersham) was employed and the 66 kiloDalton immunoreactive bands were visualized using an enhanced chemiluminescence detection kit (Amersham).

For immunocytochemistry experiments, cells grown on chamber slides were fixed in 95% ethanol for fifteen minutes and then washed twice in TBST buffer (pH 7.6) (DAKO). Endogenous peroxidase was blocked by 3% hydrogen peroxide in methanol for twenty minutes. Endogenous biotin was blocked by the Biotin Blocking System (DAKO), according to manufacturer's specifications. Slides were then incubated with the primary rabbit polyclonal antibodies against Epo (H-162, Santa Cruz Biotechnology) and EpoR (C-20, Santa Cruz Biotechnology) (1:200 dilution) overnight at 4° C. After washing five times with TBST, slides were incubated with horseradish peroxidase labeled dextran polymer coupled to anti-rabbit antibody (DAKO EnVision+System HRP) for thirty minutes at room temperature. Slides were then washed three times with TBST, developed with diaminobenzidine for ten minutes and counter-stained with hematoxylin. Negative controls included the omission of the primary antibody and primary antibody preincubated with the blocking peptide (1:10 dilution) or rhEpo (1:10 dilution) (R & D systems).

RT-PCR, Western blot and immunocytochemical analyses demonstrated that the breast carcinoma cell lines MCF-7 and BT-549 express both Epo and EpoR mRNA (FIG. 1a) and protein (FIG. 1b-d). Exposure to hypoxia stimulated Epo and to a minor extent EpoR mRNA expression in both cell lines within four hours (FIG. 1a). An increase in Epo (FIG. 1d) and EpoR (FIG. 1c-d) protein was seen in both cell lines following eight to twenty-four hours of hypoxia. Basal expression of Epo and EpoR mRNA was also detected in the human breast cancer cell lines MDA-MB-157, MDA-MB-231, MDA-MB-134, and T47-D as well as in the human prostate cell line LNCaP, and the human glioblastoma cell line MG-U87.

In all of these cells, Epo mRNA expression was markedly stimulated by hypoxia (data not shown). Basal expression of EpoR mRNA was generally much higher than that of Epo in these cell lines and hypoxia stimulated EpoR mRNA expression to a lesser extent than Epo mRNA. Nucleotide sequencing of the 449 base pair EpoR RT-PCR products obtained from MCF-7 and MG-U87 cells demonstrated that these were identical to the normal human EpoR (Winkelmann et al. (1990) Blood 76, 24-30) (BLAST NCBI search results). EpoR protein expression was markedly up-regulated by hypoxia in the MG-U87 cell line as well (data not shown). These data demonstrate that solid human tumors, such as breast carcinomas, are capable of expressing both Epo and EpoR. Furthermore, this data indicates that hypoxia stimulates the expression of not only Epo, but also EpoR protein in human cells.

Example 2

EpoR-Mediated Potentiation of DNA Synthesis

To determine whether Epo exerts trophic effects on breast cancer cell lines, the effect of exogenously added Epo on DNA synthesis was examined in MCF-7 and BT-549 cells. DNA synthesis was measured using a $^3$H-thymidine incorporation assay. Breast cancer cells plated in six well plates in one ml DMEM supplemented with 20% fetal bovine serum per well were allowed to incubate for sixteen hours. Cells were switched to one ml phenol-free DMEM at the time of treatments. recombinant human Epo (rhEpo) (10 units), or either anti-Epo or anti-EpoR antibodies (2 mg) was then added directly to the medium and the cells cultured for another sixteen hours. Thymidine labeling was performed by adding one mCi/well of $^3$H-thymidine (20 mCi/ml) (NEN Life Sciences) for one hour and DNA associated counts were then determined by liquid scintillation as described (Assandri et al. (1999) J. Physiol. 516, 343-352).

Addition of rhEpo potentiated DNA synthesis by approximately 20% in MCF-7 ($p<0.01$) and BT-549 cells ($p<0.01$) (FIG. 2). To determine whether autonomously produced Epo contributed to cell growth in an autocrine manner via EpoR activation we added anti-Epo or anti-EpoR antibodies to the culture medium. Both antibodies produced a significant inhibition of DNA synthesis (FIG. 2). Analysis of cell growth using the MTT dye reduction assay revealed similar findings in both cell lines with the respective treatments (data not shown). These data demonstrate that EpoR expression observed in the MCF-7 and BT-549 breast cancer cell lines is biologically active. Furthermore, autonomous expression of Epo and EpoR by breast cancer cells appears to constitute an autocrine signaling mechanism for cell proliferation.

Example 3

Epo and EpoR Expression in Human Breast Cancer Tissue

To investigate the potential for Epo signaling in autocrine growth and hypoxic survival of solid tumors in vivo, the expression of Epo and EpoR proteins in clinical samples of untreated breast carcinomas was examined using immunohistochemistry. For immunohistochemistry experiments, fifty cases of primary resections of untreated breast carcinomas were retrieved from the Surgical Pathology files of the University of Pennsylvania Medical Center. Immunohistochemical assays were performed on formalin-fixed paraffin-embedded sections. Five mm-thick sections were cut and de-paraffinized in xylene and rehydrated in graded alcohols. Slides were steamed in 0.01 mol/L sodium citrate buffer (pH 6.0) for twenty minutes. Blocking of endogenous peroxidase, endogenous biotin, and all subsequent staining procedures was as indicated above. Slides of human fetal liver and placenta were used as positive controls.

Figure 3:
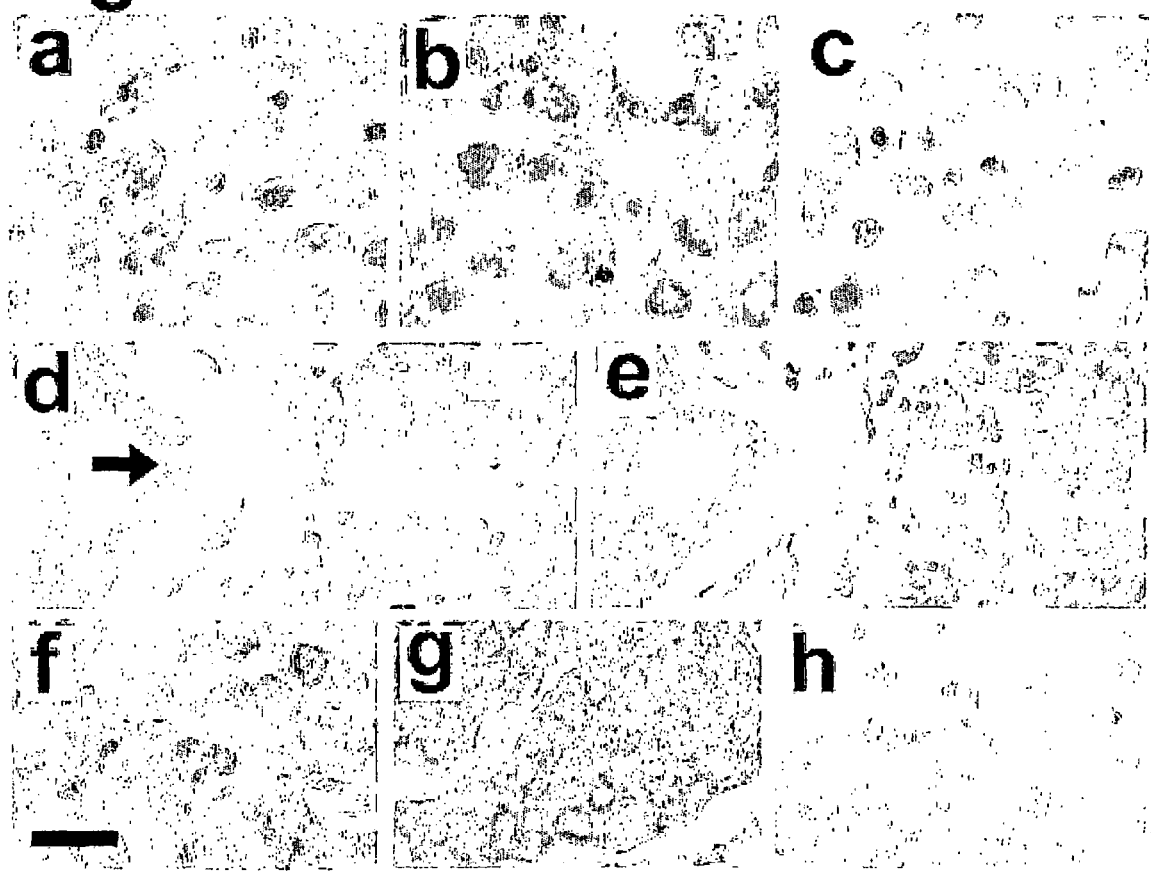
FIG. 3—Prominent expression of Epo and EpoR in human breast cancer biopsy samples. Immunohistochemical analysis of Epo (a,d,f) and EpoR (b,e,g) in paraffin sections of invasive lobular carcinoma (a-c), invasive ductal carcinoma (d,e) and ductal carcinoma in situ (DCIS, f-h) showing intense staining (brown peroxidase reaction product) associated with breast cancer cells and minimal staining of the normal breast tissue. Epo staining associated with the lumenal surface of normal ducts (arrow) was seen occasionally. All staining for EpoR was abolished when the anti-EpoR antibodies were pre-incubated with the control peptide against which the serum was raised (c, h). Pre-incubation of anti-Epo antibodies with rhEpo similarly abolished all staining for Epo (not shown). Scale bar=25 mm for (a-c) and (f-h); and 60 mm for (d,e).

High levels of Epo and EpoR expression in both lobular and ductal carcinomas was observed in all of the fifty cases examined (FIG. 3). Invasive lobular (FIG. 3a-c) and invasive ductal (FIGS. 3d,e) breast carcinomas showed prominent staining for both Epo and EpoR while normal breast tissue in all specimens examined displayed much lower immunoreactivity for Epo as well as for EpoR. Most specimens, in fact, had no detectable Epo staining associated with the normal ductal, lobular or stromal breast elements. In a few samples, low levels of Epo staining were seen associated with the lumenal aspect of normal duct cells (FIG. 3d). Even in these cases, the far more intense staining of cancer cells could easily distinguish neoplastic from normal tissue.

Figure 4:
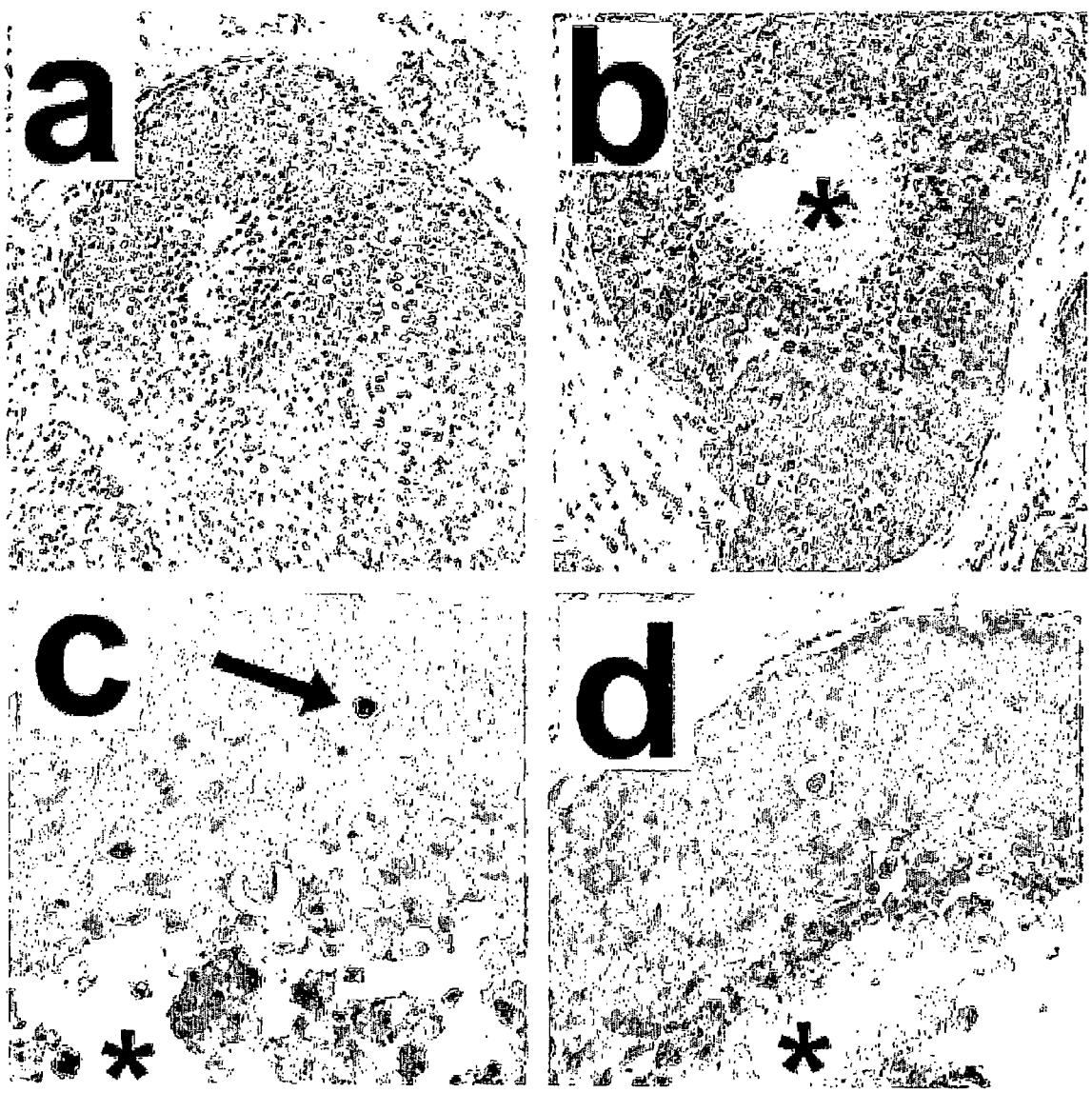
FIG. 4—Epo and EpoR expression is enhanced in hypoxic tumor regions and associated with non-apoptotic breast cancer cells. DCIS specimens with areas of comedo-like necrosis showed markedly enhanced Epo (a) and EpoR (b) staining in cancer cells which form the viable rim around the necrotic center. Double staining for apoptotic cells (brown) via the Tunel method (c,d) and Epo (c) (red) or EpoR (d) (red) demonstrates apoptotic Tunel positive apoptotic nuclei seen prominently in the border zone between necrotic (*) and viable areas of DCIS specimens and only rarely amongst the viable cells (arrow) which stain strongly for Epo (c) and EpoR (d). All staining for Epo and EpoR was abolished upon pre-incubation of the respective antiserum with rhEpo or control EpoR peptide (not shown). Scale bar=60 mm for (a,b) and 30 mm for (c,d).

Cells from invasive alveolar carcinoma and ductal carcinoma in situ (DCIS) (FIG. 3f-h) typically displayed prominent staining for EpoR throughout the lesion (FIGS. 3b,f) while Epo expression was typically heterogeneous with intense staining confined to fewer cells (FIGS. 3a,f). High grade DCIS (FIG. 4) and invasive ductal carcinomas frequently showed necrotic areas with viable rims of cancer cells. In these regions, which correspond to the most hypoxic parts of tumors, viable cancer cells demonstrated the highest levels of staining for both Epo and EpoR (FIGS. 4a,b).

Epo and EpoR expression was also correlated with apoptosis using a double staining assay. Tunel stain was performed using the ApopTag Peroxidase in situ Apoptosis Detection System (Intergen) according to the manufacturer's specifications. Sections of reactive lymph nodes with numerous apoptotic bodies in germinal centers were used as positive controls. After developing the slides with diaminobenzidine, slides were washed five times in Automation Buffer (pH 7.0) (Biomeda). After blocking with 1.5% normal goat serum (Vector Laboratories) in Automation Buffer, slides were incubated with the polyclonal antibodies against Epo and EpoR overnight at 4° C. Slides were then washed three times with Automation Buffer and incubated for thirty minutes at 37° C. with biotinylated goat anti-rabbit immunoglobulin G (heavy and light chains) secondary antibody (1:200 dilution) (Vector Laboratories). After incubation with alkaline phosphatase-conjugated streptavidin (Streptavidin AP Detection System, Research Genetics) for forty minutes at 37° C., slides were developed with stable Fast Red chromogen (Research Genetics) for ten minutes and counterstained with hematoxylin.

Higher magnification revealed a large number of apoptotic nuclei with condensed chromatin and DNA strand breaks in the tumor regions bordering necrotic and viable areas (FIGS. 4c,d). Apoptotic cells were rarely seen amongst the Epo and EpoR expressing tumor cells.

These findings have significant implications regarding multistage carcinogenesis, as well as for the diagnosis, treatment, and prevention of cancer. Hypoxia is known to select for aggressive cancer phenotypes. Experimental data demonstrating high Epo and EpoR levels in human solid tumors as well as demonstration of hypoxic up-regulation of both these proteins represents a novel way in which hypoxia may promote cancer cell proliferation. Hypoxic induction of Epo mRNA and protein expression is a well-known phenomenon (Bunn & Poyton (1996) Physiol. Rev. 76, 839-845).

EpoR induction in human cancer cells by hypoxia was far more apparent at the protein level than at the mRNA level. The enhanced expression of both Epo and EpoR mRNA as well as protein has recently been shown in rat brain following ischemic stroke (Sadamoto et al. (1998) Biochem. Biophys. Res. Comm. 253, 26-32; Bemaudin et al., (1999) J. Cereb. Blood Flow Metab. 19, 643-651), a lesion in which hypoxia would be expected to play a prominent role. However, in studies with primary cultures of rat brain cells where oxygen was the only variable, hypoxia was reported to induce only Epo mRNA and not EpoR mRNA (Bemaudin et al. (2000) Glia 30, 27 1-278). Thus hypoxia can regulate EpoR expression primarily at the level of EpoR protein stability.

The hypoxia-inducible transcription factor HIF-1 is up-regulated in such a manner under hypoxic conditions via a mechanism involving inhibition of proteasome-mediated degradation of its HIF-1 alpha subunit (Salceda & Caro (1997) J. Biol. Chem. 272, 22642-22647). Indeed, proteasome activity has also recently been shown to control the down-regulation of cell surface EpoR in Epo-stimulated cells (Verdier et al. (2000) J. Biol. Chem. 275,18375-18381). Inhibition of ubiquitin-proteasome mediated protein degradation by hypoxia may therefore represent a common signaling mechanism for the up-regulation of both HIF-1 and EpoR. HIF-1 is responsible for hypoxia-induced transcription of the Epo gene as well as for genes governing neovascularization and glycolysis, two other hallmarks of solid tumors (Semenza (1999) Ann. Rev. Cell. Dev. Biol. 15, 551-578; Carmeliet et al. (1998) Nature 394, 45-90). HIF-1 is over-expressed in common human cancers and is correlated with increased cell proliferation (Zhong et al. (1999) Cancer Res. 59, 5830-5835). Enhancement of Epo expression therefore represents a prominent cancer promoting mechanism attributable to HIF-1.

Sustained activation of EpoR by Epo is known to normally block p53-induced apoptosis in hematopoietic progenitors (Mahdi (1998) Biol. Cell 90, 615-627; Bittorf et al. (2000) Cell. Signal. 12, 23-30). Because Epo signaling has a similar function in human cancer cells, up-regulation of Epo and EpoR represents a basis for the hypoxia-mediated selection of cells with diminished apoptotic potential in solid tumors (Graeber et al. (1996) Nature 379, 88-91). Indeed, apoptotic cells amongst the Epo and EpoR expressing breast cancer cells in clinical samples were only rarely observed. Since neoplastic cells in each of the fifty cases of breast carcinoma examined were strongly positive for Epo and EpoR and since normal breast tissue was minimally reactive in all specimens, these findings indicate examination of clinical biopsies for Epo and EpoR as an aid in cancer diagnosis.

Serum from cancer patients has long been known to have erythropoietic activity (Firat & Banzon (1971) Cancer Res. 10, 1355-1359) and elevated serum Epo levels previously reported in breast cancer patients may in fact have originated from cancer cells (Shamseddine et al. (1998) Eur. J. Gynecol. Oncol. 19, 591-593). Either endogenously produced or exogenously administered Epo may therefore promote proliferation and survival of EpoR expressing cancer cells. In light of these findings, the use of rhEpo for treating anemia of chemotherapy should be preceded by examination of biopsy material for EpoR expression in order to avoid possible adverse outcome for patients. The most common reason for elevated Epo levels and secondary erythrocytosis in humans is hypoxia caused by cigarette smoking (Sagone & Balcarzak (1975) Ann. Intern. Med. 82, 512-515; Varvarigou et al. (1994) J. Pediatr. 124,480-482). Our findings thus also suggest another mechanism linking smoking with cancer promotion (Johnson et al. (2000) Cancer Causes Control 11, 211-221).

Example 4

Epo and EpoR Expression in Human Cervical Cancer Tissue

The recent demonstration of estrogen-stimulated Epo expression in the female reproductive tract prompted the examination of the expression of Epo and EpoR in human cervical cancer. A total of sixty cervical biopsy or hysterectomy specimens were examined. The histologic diagnosis included invasive squamous cell carcinoma (SSC) (n=9), severe squamous dysplasia (SD) (n=16), moderate SD (n=8), mild SD (n=10), condyloma without SD (n=18).

Formalin-fixed, paraffin-embedded tissue was immunostained with polyclonal antibody against erythropoietin receptor (EpoR) after heat induced antigen retrieval (1:250 dilution, C-20 rabbit polyclonal, Santa Cruz Biotechnologies Inc.) using the DAKO EnVision+System HRP, Rabbit. Slides of human placenta were used as positive controls. Negative controls included the omission of the primary antibody and primary antibody preincubated with blocking peptide for EpoR (10:1 peptide: antibody ratio). Immunohistochemical stains for EpoR were interpreted semiquantitatively by assessing the intensity of staining according to a four-tiered scale. First, the total percentage of positively staining epithelial cells was assessed. Then the percentage of weakly, moderately and strongly staining cells was determined, such that the sum of these categories equated with the overall percentage of positivity. A staining score was then calculated as follows: Score (out of maximum of 300)=sum of 1×percentage of weak, 2×percentage of moderate and 3×percentage of strong staining.

For the comparison of EpoR expression in squamous dysplasia, squamous cell carcinomas and the corresponding benign epithelial cells the Wilcoxon signed rank test was used. For the comparison of benign epithelial cells, different grades of dysplasia and squamous cell carcinoma, the Kruskal-Wallis one-way analysis of variance by ranks was used, followed by Dunn's multiple comparison test. A two-sided p-value less than 0.05 was considered statistically significant.

The results of immunochemical staining of normal, benign cancerous and malignant cancerous cervical epithelial samples appear below in tabular form.

Expression of EpoR in benign cervical epithelium, squamous dysplasias and invasive squamous cell carcinomas of the cervix

| Histologic diagnosis | N | EpoR immunostaining score | | |
|---|---|---|---|---|
| | | Median | Range | Mean ± SEM |
| Benign endocervical epithelium | 47 | 0 | 0-50 | 6.4 ± 1.9 |
| Benign squamous epithelium | 55 | 20 | 0-50 | 15.6 ± 1.3 |
| Immature squamous metaplasia | 6 | 15 | 10-60 | 25.0 ± 8.5 |
| HPV without dysplasia | 43 | 10 | 0-60 | 16.7 ± 2.2 |
| Mild squamous dysplasia | 10 | 45 | 30-60 | 45.9 ± 4.5 |
| Moderate squamous dysplasia | 8 | 100 | 60-120 | 92.5 ± 9.9 |
| Severe squamous dysplasia | 16 | 180 | 90-270 | 164.4 ± 13.4 |
| Invasive squamous cell carcinoma | 9 | 190 | 100-200 | 170.0 ± 13.6 |

The results may also be summarized as follows. In normal squamous epithelium, EpoR expression was found in the basal one or two cell layers, while mature squamous cells and endocervical epithelial cells did not show EpoR expression. No immunostaining was seen in areas of condyloma without squamous dysplasia. Weak, focal EpoR expression was found in benign endocervical epithelium in 6 of 47 (12.7%) cases. EpoR expression in areas of HPV changes without dysplasia was similar to that seen in benign squamous epithelium. In cases of cervical intraepithelial neoplasia, weak to moderate EpoR staining was seen in the dysplastic squamous cells; the adjacent non-dysplastic epithelium lacked EpoR expression.

A statistically significant increase in EpoR expression was found when the level of staining in all groups of squamous dysplasia (SD) or in invasive squamous cell carcinoma (SCC) was compared to the groups benign squamous epithelium, benign endocervical epithelium or HPV changes without dysplasia. The increased expression of EpoR in SD and SCC may represent an adaptive response of the tumors and may contribute to their proliferation. The level of EpoR staining correlated well with the degree of squamous dysplasia ($p<0.0001$, $r^2=0.5464$, slope=29.2, test for linear trend). Diffuse moderate EpoR expression was found in cases of invasive squamous cell carcinoma.

Example 5

Human Breast Cancer Cell Lines Express Functional EpoR

Figure 5:
FIG. 5—Human breast cancer cell lines express functional erythropoietin receptor. (a) The human breast cancer cell lines MDA-231 (1), MDA-134 (2), and T4D7 (3) all express a strongly immunoreactive band at approximately 66 kDa identified with the anti-EpoR antibody. (b) Staining of this band in all cell lines was specifically abolished when antibody was pre-incubated with the EpoR peptide (+) against which the antiserum was raised as shown here for the human breast cancer cell lines MCF-7 and BT-549. (c) The basal levels (1) of phosphotyrosine containing proteins in MCF-7 cells were markedly enhanced following a five minute incubation with either 250 units/ml of rhEpo (2) or 10 µM Epo mimetic peptide (3). (d) $^3$H-thymidine incorporation into both MCF-7 and BT-549 cell lines was enhanced by about 25% upon addition of 10 units/ml exogenous rhEpo to the media. (**$p<0.01$, one tailed T-test).

The human breast cancer cell lines MDA-231, MDA-134 and T4D7 all express a strongly immunoreactive band at approximately 66 kDa identified with the anti-EpoR antibody (FIG. 5). Staining of this band in all cell lines was specifically abolished when antibody was pre-incubated with the EpoR peptide against which the antiserum was raised as shown for the human breast cancer cell lines MCF-7 and BT-549. The basal levels of phosphotyrosine containing proteins in MCF-7 cells were markedly enhanced following a five minute incubation with either 250 units/ml of rhEpo or Epo mimetic peptide. $^3$H-thymidine incorporation into both MCF-7 and BT-549 cell lines was enhanced by about 25% upon addition of 10 units/ml exogenous rhEpo to the media.

Example 6

Figure 6:
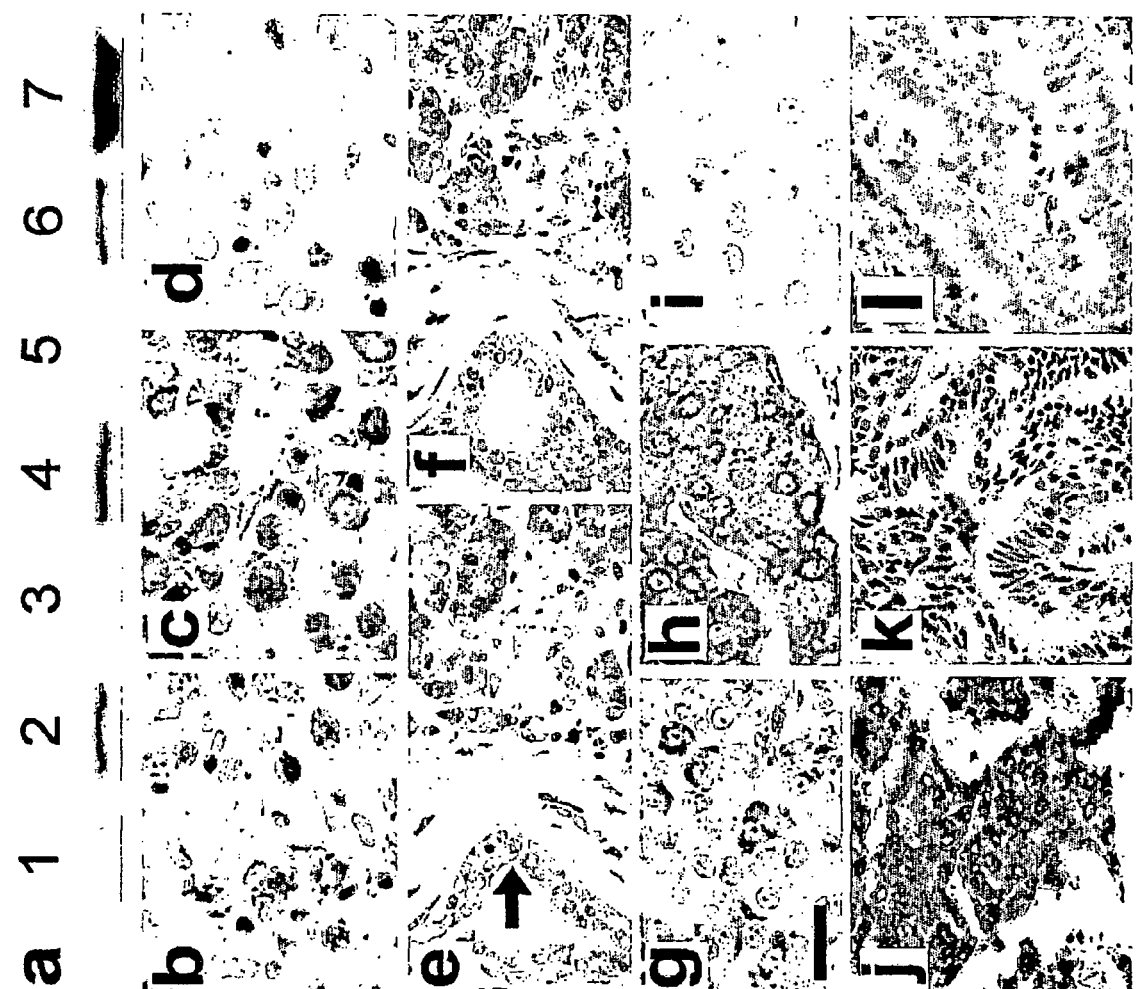
FIG. 6—Enhanced expression of Epo and EpoR in human breast cancer biopsies clearly distinguishes neoplastic from benign tissue. (a) Western blot analysis for EpoR expression in frozen biopsy samples shows immunoreactivity in cancerous tissue: (1) cancer, (2) cancer, (3) non-cancerous breast tissue biopsied adjacent to sample (2), (4) cancer, (5) non-cancerous breast tissue adjacent to sample (4), (6) cancer, (7) breast cancer specimen post chemotherapy. (b-i) Immunohistochemical analysis of EpoR and Epo in paraffin sections of invasive lobular carcinoma (b-d), invasive ductal carcinoma (e,f) and ductal carcinoma in situ (DCIS, g-i) showing intense staining (brown peroxidase reaction product) associated with breast cancer cells and minimal staining of the normal breast tissue (arrow). (j-k) Marked enrichment of EpoR in ductal carcinoma cells (j) as compared with benign hyperplastic cells (k) stained in the same specimen on the same slide. (1) Another example of low EpoR staining in a specimen with benign hyperplasia. All staining for EpoR was abolished when the anti-EpoR antibodies were pre-incubated with the control peptide against which the serum was raised (d,i). Pre-incubation of anti-Epo antibodies with Epo peptide similarly abolished all staining for Epo (not shown).

Enhanced Expression of Epo and EpoR in Human Breast Cancer Biopsies Clearly Distinguishes Neoplastic from Benign Tissue Western blot analysis for EpoR expression in frozen biopsy samples demonstrated immunoreactivity in cancerous tissue (FIG. 6) when compared to non-cancerous breast tissue biopsied adjacent to the sample and breast cancer specimens post-chemotherapy. Immunohistochemical analysis of EpoR and Epo in paraffin sections of invasive lobular carcinoma, invasive ductal carcinoma and ductal carcinoma in situ (DCIS) displayed intense staining (brown peroxidase reaction product) associated with breast cancer cells and minimal staining of the normal breast tissue. Marked enrichment of EpoR in ductal carcinoma cells was observed when compared with benign hyperplastic cells stained in the same specimen on the same slide. All staining for EpoR was abolished when the anti-EpoR antibodies were pre-incubated with the control peptide against which the serum was raised. Pre-incubation of anti-Epo antibodies with Epo peptide similarly abolished all staining for Epo.

Example 7

Increased Expression of Epo in Breast Tumor Biopsies is Diagnostic for Carcinomas in Non-Smokers and for Malignant and Benign Tumors in Smokers, While Increase Expression of EpoR is Diagnostic for Carcinomas Epo protein levels in 184 breast biopsy specimens containing 158 in situ and 184 invasive mammary carcinomas were determined. Hematoxylin and eosin stained slides were reviewed to confirm the diagnosis, including histological type and tumor grade, based on established criteria (Elston et al. (1998) The Breast, Churchill Livingstone, pp. 283-337; Page et al. (1987) Diagnostic Histopathology of the Breast, W. B. Saunders, pp. 193-235; Rosen et al. (1993) Tumors of the Mammary Gland, Atlas of Tumor Pathology). Ductal carcinomas in situ were graded as described by Scott et al. (1997) Hum. Pathol. 28, 967-973), using primarily nuclear grade. All invasive carcinomas were graded using the modified combined histological grading system as described by Elston et al. (1998) The Breast, Churchill Livingstone, pp. 365-384. Tumors were also evaluated to determine the presence or absence of tumor necrosis and lymphovascular invasion. Information regarding tumor staging, including tumor size, axillary lymph node involvement, and other therapeutic and prognostic biologic markers, such as estrogen and progesterone receptor status and erbB-2 overexpression, were retrieved from the pathology reports. Smoking history was collected from a standardized questionnaire on 102 individuals who participated in both the present study and in a separate study of breast cancer risk factors.

Immunohistochemical assays were performed on formalin-fixed paraffin-embedded sections. Five micron sections were cut, deparaffinized in xylene and rehydrated in graded alcohols. Slides were steamed in 0.01 mol/L sodium citrate buffer (pH 6.0) for twenty minutes, and endogenous peroxidase activity was blocked by 3% hydrogen peroxide in methanol for twenty minutes. Slides were then incubated with the polyclonal antibody against erythropoietin (rabbit polyclonal H-162, 1:200 dilution, Santa Cruz Biotechnology) and erythropoietin receptor (rabbit polyclonal C-20, 1:200 dilution, Santa Cruz Biotechnology) overnight at 4° C. Next, the slides were washed five times with Tris Buffered Saline containing Tween 20 (TBST) and incubated for thirty minutes at room temperature with horseradish peroxidase-labeled dextran polymer coupled to anti-rabbit antibody (EnVision+System HRP, DAKO). Slides were then washed three times with TBST, developed with stable diaminobenzidine (Research Genetics) for ten minutes and counterstained with hematoxylin. Slides of fetal liver (24) and placenta (27) were used as positive controls. A negative control was included in each case by omission of the primary antibody. The specificity of the immunoreactivity was evaluated by an antibody absorption test: the primary antibody was preincubated with blocking peptide for EpoR (Santa Cruz Biotechnology) or human recombinant Epo (10:1 peptide:antibody ratio) (R & D Systems).

Immunohistochemical stains for Epo and EpoR were interpreted semiquantitatively by assessing the intensity of staining according to a four-tiered scale. First, the total percentage of positive tumor cells and benign ductal and lobular epithelial cells was assessed. Then, the percentage of weakly, moderately and strongly staining cells was determined, so that the sum of these categories equated with the overall percentage of positivity. A staining score was calculated as follows: Score (out of maximum of 300)=sum of 1×percentage of weak, 2×percentage of moderate and 3×percentage of strong staining. In addition, a differential tumor score (DTS) was also calculated by subtracting the staining score of the adjacent benign epithelium from that of the in situ and invasive carcinomas. Immunohistochemical stains were evaluated independently by two pathologists. Slight differences in interpretation were resolved by simultaneous viewing.

The Wilcoxon signed rank test was used for the comparison of median Epo and EpoR expression levels in carcinomas and the adjacent benign mammary epithelial cells. The correlation between the levels of Epo and EpoR staining in invasive and in situ components of carcinomas was estimated using the Spearman rank correlation test. We examined the correlation between median Epo and EpoR expression levels and tumor type, size, combined tumor grade, lymph node status, estrogen and progesterone receptor status and erbB-2 overexpression. For the statistical analysis, the Mann-Whitney rank sum test and the Kruskal-Wallis one-way analysis of variance by ranks was used, followed by Dunn's multiple comparison test, when appropriate. Statistical significance was determined if the two-sided p value of a test was less than 0.05.

In benign mammary epithelial cells adjacent to tumor we found weak to moderate granular cytoplasmic staining for Epo in 169 of 184 (91.8%) cases. Epo staining was usually most pronounced at the apical part of epithelial cells in the lobules. We found prominent, strong Epo expression in lobules showing secretory change. In benign epithelial lesions, including usual hyperplasia without atypia, sclerosing adenosis and papillomas, Epo expression was similar to that in normal ductal and lobular epithelial cells. Epo expression was found in 112 of 122 (91.8%) ductal carcinomas in situ (DCIS) and in 34 of 36 (94.4%) lobular carcinomas in situ (LCIS) (Table 1). Similarly, Epo expression was detected in 174 of 184 (94.6%) of invasive breast carcinomas (Table 2). Epo staining was usually weak to moderate and heterogeneous. However, strong, prominent staining was present in viable tumor cells adjacent to necrotic areas and at the infiltrating edge of carcinomas. Necrotic tissue showed no Epo after staining. Epo expression was similar in the in situ and invasive components of the tumors (r=0.844, p<0.0001, Spearman rank correlation test).

Compared to the benign epithelial cells, Epo expression was significantly increased in DCIS (p<0.0001, Wilcoxon signed rank test, rs=0.683, p<0.0001), LCIS (p<0.005, Wilcoxon signed rank test, rs=0.477, p<0.005) and invasive carcinomas (p<0.0001, Wilcoxon signed rank test, rs=0.731, p<0.0001). Interestingly, when smokers (n=61) and non-smokers (n=41) were analyzed separately, a significant difference in Epo expression between invasive carcinomas and benign epithelial cells was determined only in non-smokers (p=0.0018, Wilcoxon signed rank test, rs=0.816, p<0.0001), but not in smokers (p>0.05, Wilcoxon signed rank test, rs=0.703, p<0.0001). Similarly, while Epo expression was significantly higher in DCIS compared to benign epithelial cells in non-smokers (p<0.001, n=30, Wilcoxon signed rank test, rs=0.733, p<0.0001), the difference was only marginally significant in smokers (p=0.0444, n=35, Wilcoxon signed rank test, rs=0.687, p<0.0001). Although Epo expression was increased in benign epithelial cells in smokers (median score: 100; mean±SEM: 90.2±7.3; n=61) compared to non-smokers (median score: 60; mean±SEM: 79.0±10.1; n=41), this did not reach statistical significance (p>0.05, Mann-Whitney test).

Compared to normal controls, Epo expression was increased in invasive ductal and lobular carcinomas and in carcinomas with mixed ductal and lobular features (p>0.05, Kruskal-Wallis test) (Table 2). Although each type of carcinoma showed an elevated level of Epo expression, there was no significant difference in level among the types. Similarly, no difference was found in Epo expression between DCIS and LCIS (p>0.05, Mann-Whitney test). There was no correlation between Epo expression and tumor size, grade, presence of tumor necrosis, lymphovascular invasion, nodal status, estrogen and progesterone receptor status and erbB-2 overexpression (p>0.05, Kruskal-Wallis or Mann-Whitney test, Table 2). Similarly, no correlation was found between Epo expression and grade of DCIS or presence of comedo-type necrosis (p>0.05, Kruskal-Wallis or Mann-Whitney test, Table 1).

Interestingly, when the analysis was done using the differential tumor scores for Epo, we found a significant correlation between increased Epo expression in the tumors and the presence of nodal metastases (p=0.0397, Mann-Whitney test) (Table 2). In addition, when Epo expression in DCIS and invasive carcinoma was compared to the adjacent benign epithelium in the same specimens, we found significantly higher Epo staining in intermediate (p<0.01) and high grade (p<0.0001) tumors only, but not in low grade carcinomas (p>0.05, Wilcoxon signed rank test).

Diffuse, moderate to strong cytoplasmic and membrane expression of EpoR was seen in 121 of 122 (99.2%) DCIS, 36 of 36 (100%) LCIS, and 183 of 184 (99.5%) invasive carcinomas. Although EpoR staining was usually uniform throughout the tumor, increased expression was seen in tumor cells adjacent to necrotic areas. Necrotic tissue itself showed no staining for EpoR. EpoR expression was similar in the in situ and invasive components of the tumors (r=0.795, p<0.0001, Spearman rank correlation test). In addition, strong EpoR expression was found in the tumor vasculature.

Compared to benign epithelial cells EpoR expression was significantly increased in DCIS (p<0.0001, Wilcoxon signed

TABLE 1

Epo expression in in situ mammary carcinomas

| | In situ carcinoma | n | Epo Staining Score | | | Epo DTS* | | |
|---|---|---|---|---|---|---|---|---|
| | | | Median | Mean ± SEM | p** | Median | Mean ± SEM | p** |
| Type | DCIS | 122 | 90 | 90.3 ± 6.4 | >.05 | 5 | 26.4 ± 4.9 | >.05 |
| | LCIS | 36 | 100 | 97.9 ± 9.5 | | 0 | 25.7 ± 8.4 | |
| DCIS Grade | Low | 22 | 60 | 79.6 ± 15.7 | >.05 | 7.5 | 18.8 ± 11.1 | >.05 |
| | Intermediate | 51 | 80 | 91.5 ± 10.2 | | 0 | 24.3 ± 8.2 | |
| | High | 49 | 100 | 96.0 ± 9.9 | | 17.5 | 33.4 ± 8.0 | |
| Necrosis | Absent | 59 | 95 | 91.3 ± 9.4 | >.05 | 5 | 27.1 ± 8.2 | >.05 |
| | Present | 63 | 90 | 92.8 ± 8.9 | | 10 | 27.4 ± 6.4 | |

*Epo differential tumor score (DTS): Epo staining score of tumor minus Epo staining score of corresponding benign epithelium;
**Mann-Whitney or Kruskal-Wallis test

TABLE 2

Epo expression in invasive mammary carcinomas

| | IMC | n | Epo Staining Score | | | Epo DTS* | | |
|---|---|---|---|---|---|---|---|---|
| | | | Median | Mean ± SEM | p** | Median | Mean ± SEM | p** |
| Total | | 184 | 80 | 80.8 ± 4.9 | N/A | 0 | 14.5 ± 3.6 | N/A |
| Type | Ductal | 126 | 70 | 78.3 ± 6.3 | >0.05 | 0 | 13.5 ± 4.5 | >0.05 |
| | Mixed | 27 | 80 | 74.4 ± 11.9 | | 0 | 11.8 ± 10.2 | |
| | Lobular | 31 | 100 | 96.5 ± 9.9 | | 0 | 20.7 ± 7.5 | |
| Grade | I | 44 | 90 | 88.2 ± 10.5 | >0.05 | 0 | 7.3 ± 5.9 | >0.05 |
| | II | 89 | 80 | 81.7 ± 6.6 | | 2 | 13.7 ± 3.8 | |
| | III | 51 | 70 | 73.5 ± 10.3 | | 0 | 20.3 ± 8.9 | |
| Size | T1 | 91 | 35 | 62.4 ± 12.3 | >0.05 | 0 | 6.2 ± 4.1 | >0.05 |
| | T2-4 | 93 | 70 | 77.6 ± 6.9 | | 0 | 19.3 ± 5.6 | |
| Tumor necrosis | Absent | 141 | 80 | 81.7 ± 5.6 | >0.05 | 0 | 10.6 ± 3.3 | >0.05 |
| | Present | 43 | 70 | 77.9 ± 10.7 | | 5 | 27.2 ± 10.1 | |
| Lymphovascular invasion | Absent | 119 | 80 | 80.7 ± 6.3 | >0.05 | 0 | 11.1 ± 4.5 | >0.05 |
| | Present | 65 | 80 | 80.7 ± 8.2 | | 0 | 17.0 ± 4.7 | |
| Nodal status | Negative | 95 | 75 | 80.8 ± 7.6 | >0.05 | 0 | 10.4 ± 4.6 | 0.0397 |
| | Positive | 89 | 90 | 84.1 ± 6.9 | | 10 | 22.6 ± 5.6 | |
| ER status | Negative | 75 | 80 | 84.4 ± 7.9 | >0.05 | 0 | 22.8 ± 7.4 | >0.05 |
| | Positive | 109 | 70 | 77.4 ± 6.6 | | 0 | 10.7 ± 3.2 | |
| PR status | Negative | 77 | 80 | 80.6 ± 7.7 | >0.05 | 0 | 13.6 ± 5.0 | >0.05 |
| | Positive | 107 | 70 | 80.4 ± 6.7 | | 0 | 16.9 ± 5.3 | |
| ErbB-2 status | Negative | 116 | 80 | 87.8 ± 5.9 | >0.05 | 0 | 12.6 ± 4.5 | >0.05 |
| | Positive | 68 | 75 | 68.6 ± 8.8 | | 1 | 16.8 ± 5.2 | |

*Epo diferential tumor score (DTS): Epo staining score of tumor minus Epo staining score of corresponding benign epithelium;
**Mann-Whitney or Kruskal-Wallis test In normal ductal and lobular epithelial cells adjacent to tumor weak, granular cytoplasmic EpoR expression was seen in 176 of 184 (95.6%) cases. In contrast to Epo expression, no increased EpoR staining was seen in lobules showing secretory changes. Benign epithelial lesions, including usual hyperplasia, sclerosing adenosis and benign papillomas showed weak EpoR expression similar to that seen in normal epithelial cells.

rank test, rs=0.467, p<0.0001), LCIS (p<0.0001, Wilcoxon signed rank test, rs=0.483, p<0.005) and invasive carcinomas (p<0.0001, Wilcoxon signed rank test, rs=0.355, p<0.0001) (Table 3 and Table 4). EpoR expression in DCIS and invasive carcinomas was significantly higher compared to benign epithelial cells both in non-smokers (DCIS: n=30, p<0.0001, rs=0.331, p<0.05; invasive carcinomas: n=41, p<0.0001, rs=0.420, p<0.005, Wilcoxon signed rank test) and in smokers (DCIS: n=35, p<0.0001, rs=0.608, p<0.0001; invasive carcinomas: n=61, p<0.0001, rs=0.494, p<0.0001, Wilcoxon signed rank test). There was no difference in the expression of EpoR in benign epithelial cells between non-smokers (median score: 100; mean±SEM: 85.3±9.9; n=41) and smokers (median score: 100; mean±SEM: 95.6±6.6; n=61) (p>0.05, Mann-Whitney test).

EpoR was expressed at elevated levels in DCIS and LCIS samples, as well as in invasive ductal and lobular carcinomas and invasive carcinomas with mixed ductal and lobular features. Based on the EpoR staining scores, however, no significant difference in EpoR expression level was found between DCIS and LCIS, or among the level in invasive ductal and lobular carcinomas and carcinomas with mixed ductal and lobular features (p>0.05, Kruskal-Walis test) (Table 4). On the other hand, based on the differential tumor scores, a highly significant difference in EpoR expression was seen between ductal and lobular carcinomas. Higher levels of staining were observed in ductal samples, with lower levels in lobular samples. Mixed tumors showed intermediate levels of EpoR staining (p<0.0001, Kruskal-Wallis test) (Table 4). A similar difference was found in EpoR expression between DCIS and LCIS samples as well (p=0.0066, Mann-Whitney test) (Table 3).

No correlation was found between EpoR expression level and tumor size (p>0.05, Mann-Whitney test). In DCIS, a significant correlation was seen between EpoR expression and tumor grade and the presence of tumor necrosis (Table 3). Similarly, in invasive carcinomas, a significantly higher level of EpoR expression was seen in carcinomas with a high combined histologic grade, in carcinomas showing tumor necrosis and lymphovascular invasion and in tumors associated with lymph node metastases (Table 4). EpoR staining was also significantly higher in breast carcinomas negative for estrogen and progesterone receptor expression compared with hormone receptor positive tumors (Table 4). No correlation was found between EpoR expression and erbB-2 overexpression by the tumors (Table 4).

TABLE 3

In situ EpoR expression in mammary carcinomas

| In situ carcinoma | | n | EpoR Staining Score | | | EpoR DTS* | | |
|---|---|---|---|---|---|---|---|---|
| | | | Median | Mean ± SEM | p** | Median | Mean ± SEM | p** |
| Type | DCIS | 122 | 200 | 175.7 ± 6.8 | >.05 | 100 | 95.1 ± 6.3 | .0066 |
| | LCIS | 36 | 115 | 164.5 ± 10.3 | | 40 | 58.4 ± 10.0 | |
| DCIS Grade | Low | 22 | 95 | 149.0 ± 16.9 | .0041 | 60 | 63.5 ± 13.1 | .0111 |
| | Intermediate | 51 | 105 | 164.4 ± 10.3 | | 100 | 89.6 ± 9.8 | |
| | High | 49 | 160 | 204.1 ± 9.3 | | 100 | 120.8 ± 9.8 | |
| Necrosis | Absent | 59 | 115 | 162.4 ± 9.1 | .03 | 100 | 89.5 ± 7.9 | >.05 |
| | Present | 63 | 140 | 194.8 ± 9.1 | | 100 | 112.3 ± 9.1 | |

*EpoR differential tumor score (DTS): EpoR staining score of tumor minus EpoR staining score of corresponding benign epithelium;
**Mann-Whitney or Kruskal-Wallis test

TABLE 4

EpoR expression in invasive mammary carcinomas

| IMC | | n | EpoR Staining Score | | | EpoR DTS* | | |
|---|---|---|---|---|---|---|---|---|
| | | | Median | Mean ± SEM | P** | Median | Mean ± SEM | P** |
| Total | | 184 | 190 | 172.5 ± 5.3 | N/A | 100 | 93.0 ± 5.3 | N/A |
| Type | Ductal | 126 | 185 | 176.7 ± 6.5 | >.05 | 100 | 106.0 ± 5.9 | <.0001 |
| | Mixed | 27 | 200 | 166.3 ± 15.2 | | 100 | 86.6 ± 17.4 | |
| | Lobular | 31 | 200 | 161.0 ± 10.3 | | 40 | 46.0 ± 9.4 | |
| Grade | I | 44 | 155 | 149.3 ± 10.6 | .026 | 60 | 63.9 ± 10.9 | .0003 |
| | II | 89 | 200 | 177.0 ± 7.4 | | 100 | 96.4 ± 6.9 | |
| | III | 51 | 195 | 183.6 ± 10.0 | | 120 | 117.1 ± 8.3 | |
| Size | T1 | 91 | 180 | 159.2 ± 8.2 | >.05 | 90 | 87.0 ± 7.6 | >0.05 |
| | T2-4 | 93 | 195 | 178.0 ± 6.8 | | 100 | 95.6 ± 6.5 | |
| Tumor necrosis | Absent | 141 | 180 | 165.4 ± 6.0 | .027 | 90 | 84.8 ± 5.8 | .0123 |
| | Present | 43 | 200 | 193.3 ± 10.3 | | 110 | 113.9 ± 9.2 | |
| Lymphovascular invasion | Absent | 119 | 170 | 161.3 ± 6.9 | .0069 | 80 | 79.9 ± 6.5 | .0061 |
| | Present | 65 | 200 | 189.8 ± 7.5 | | 110 | 107.1 ± 7.4 | |
| Nodal status | Negative | 95 | 170 | 160.8 ± 7.8 | .0075 | 85 | 80.4 ± 7.6 | >.05 |
| | Positive | 89 | 200 | 187.5 ± 7.0 | | 100 | 101.6 ± 7.0 | |
| ER status | Negative | 75 | 200 | 185.7 ± 7.9 | .0375 | 100 | 108.3 ± 7.2 | .0115 |
| | Positive | 109 | 180 | 161.3 ± 6.9 | | 90 | 80.4 ± 6.7 | |
| PR status | Negative | 77 | 200 | 185.9 ± 7.6 | .0404 | 100 | 101.4 ± 7.3 | >.05 |
| | Positive | 107 | 170 | 161.1 ± 7.1 | | 100 | 89.2 ± 6.8 | |
| ErbB-2 status | Negative | 116 | 180 | 175.3 ± 6.8 | >.05 | 100 | 93.2 ± 6.8 | >.05 |
| | Positive | 68 | 190 | 164.6 ± 8.6 | | 100 | 93.4 ± 7.6 | |

*EpoR diferential tumor score DTS): EpoR staining score of tumor minus EpoR staining score of corresponding benign epithelium;
**Mann-Whitney or Kruskal-Wallis test

Example 8

Hypoxia Stimulates Epo and EpoR Expression in Breast Cancer

Figure 7:
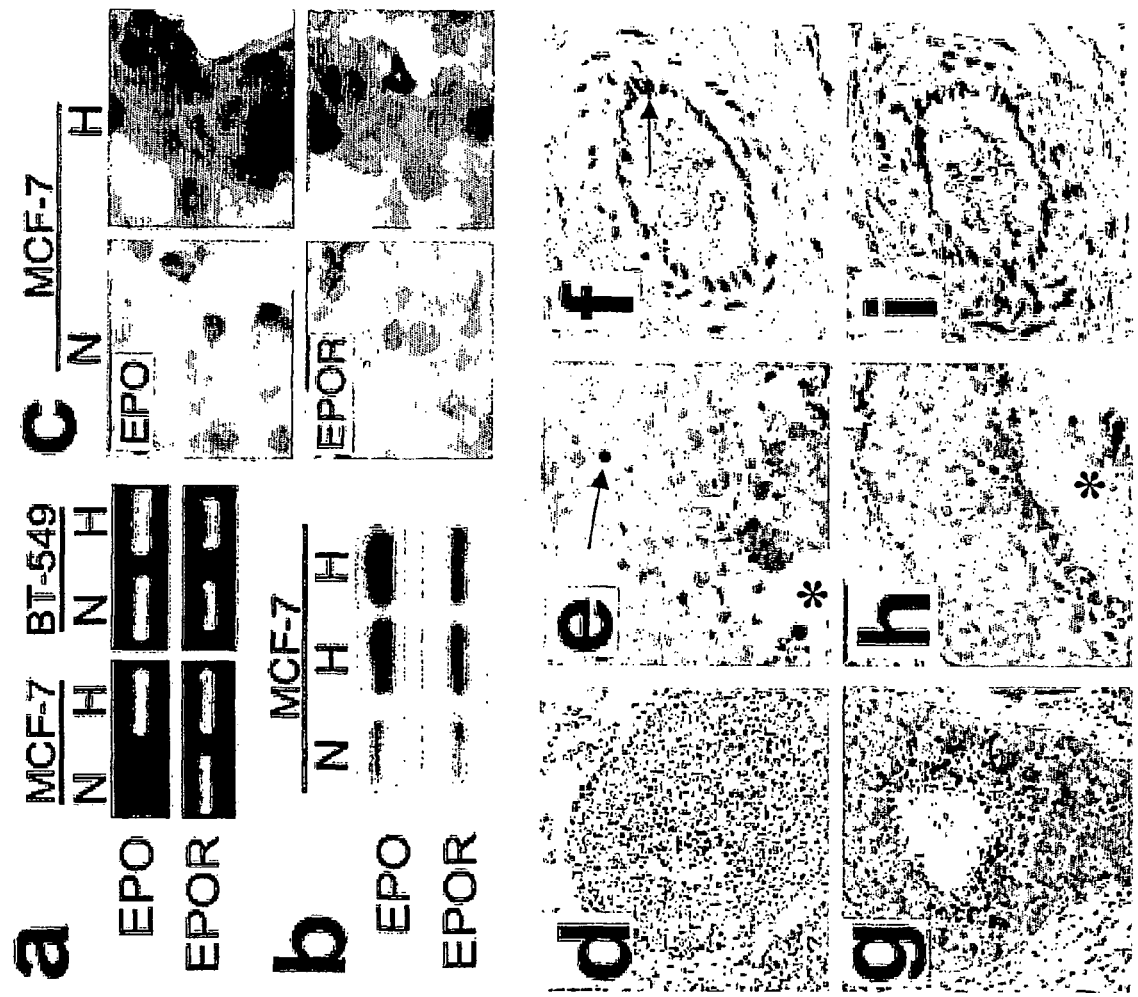
FIG. 7—Hypoxia stimulates Epo and EpoR expression in breast cancer. (a) Both the MCF-7 and BT-549 cell lines demonstrated stimulation of Epo mRNA expression via RT-PCR analysis following exposure to hypoxia (1% oxygen) for twenty-four hours (H) when compared to normoxic cultures (N). EpoR mRNA did not change prominently in hypoxic (N). (b) Hypoxia did enhance expression of both Epo and EpoR at the protein level. Two independent hypoxic MCF-7 samples (H) are compared with a normoxic sample (N) in this figure. (c) The basal expression of Epo and EpoR in MCF-7 cultures was localized to a fraction of the cells via immunoreactivity while hypoxia induced prominent staining of nearly all cells. Similar results were seen with BT-549 cells (data not shown). (d,g) DCIS specimens with areas of comedo-like necrosis showed markedly enhanced Epo (d) and EpoR (g) staining in the cells forming the viable rim around the necrotic center. (e,h) Double staining of DCIS samples for Epo (e) or EpoR (h) (both stained red in these panels) and apoptotic nuclei via the Tunel method (brown). Tunel positive apoptotic nuclei are seen prominently in the border zone between necrotic (*) and viable areas of DCIS specimens and only rarely amongst the viable cells (arrow) which stain strongly for Epo (e) and EpoR (h). (f,i) Epo and EpoR staining of tumor vasculature. Blood vessels in the tumor samples showed immunoreactivity for Epo (f) associated predominantly with the endothelium (arrow) while EpoR staining (i) was strongly seen in the endothelium and smooth muscle cells. All staining for EpoR and Epo was abolished upon pre-incubation of the respective antiserum with the control EpoR peptide or Epo peptide (not shown).
Figure 8:
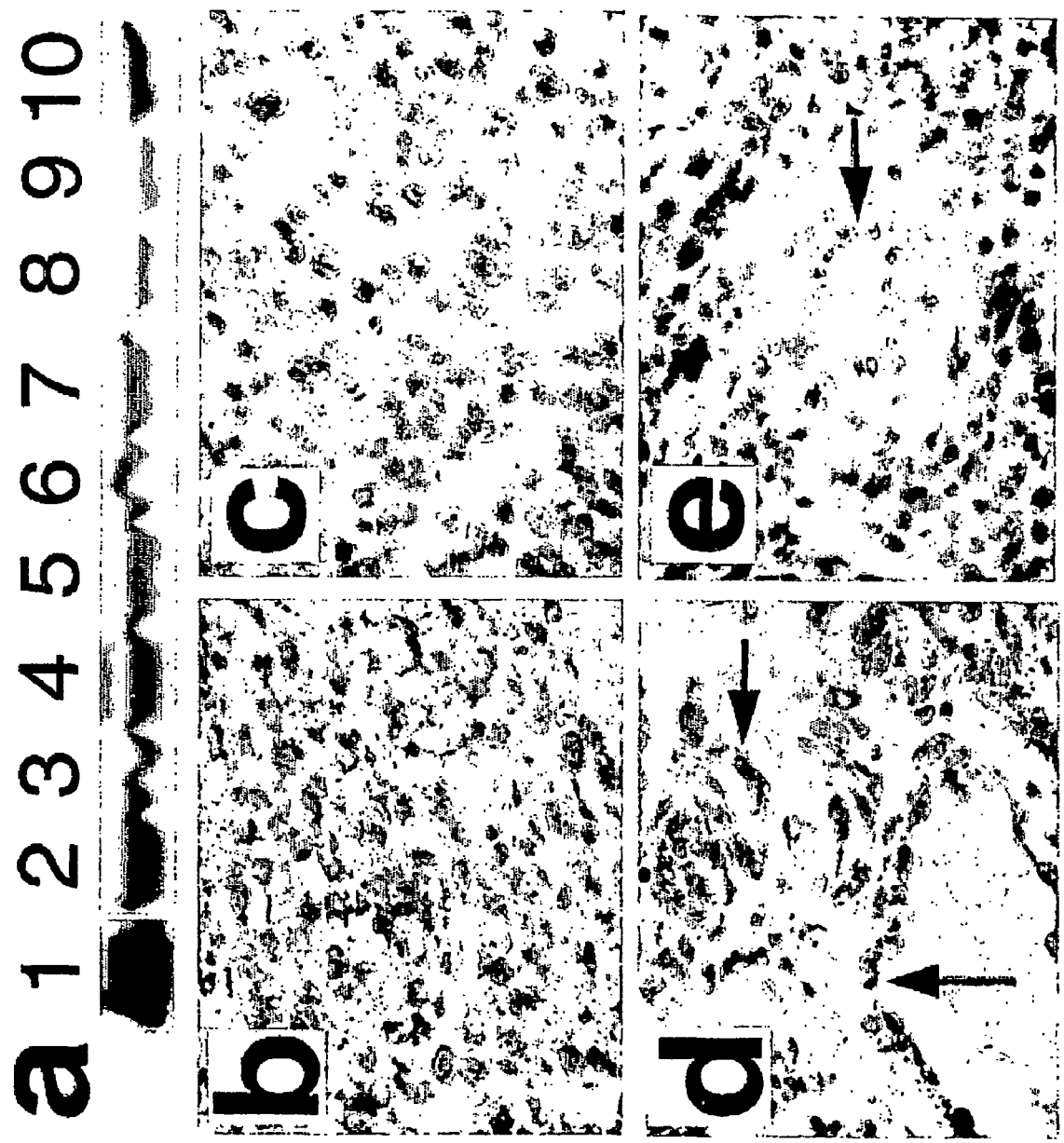
FIG. 8—Human solid cancers express EpoR and Epo. (a) Western blot analysis showing strong expression of EpoR in several human cell lines: (1) UT-7 erythrocytic leukemia cells, (2) HEP3B hepatoma cells, (3) Hela cervical carcinoma cells, (4) SHSY5Y Neuroblastoma cells, (5) U87 glioblastoma cells, (6) U251 glioma cells, (7) U373 Glioma cells, (8) Frozen specimen from ovarian cancer, (9) Frozen specimen from metastatic ovarian cancer, (10) Frozen sample of lung cancer. (b,c) Expression of EpoR (b) and Epo (c) in medulloblastoma biopsy specimen. (d,e) Expression of EpoR (d) and Epo (e) in tumor vasculature. Staining for EpoR is associated with endothelium of arteriole (vertical arrow) and capillaries (horizontal arrow) but not with smooth muscle. Epo staining is only faintly seen in endothelium.

Both the MCF-7 and BT-549 cell lines demonstrated stimulation of Epo mRNA expression via RT-PCR analysis following exposure to hypoxia (1% oxygen) for twenty-four hours when compared to normoxic cultures (FIG. 7). EpoR mRNA did not change prominently in hypoxic cells. Hypoxia did enhance expression of both Epo and EpoR at the protein level based on two independent hypoxic MCF-7 samples were compared with normoxic samples. The basal expression of Epo and EpoR in MCF-7 cultures was localized to a fraction of the cells via immunoreactivity while hypoxia induced prominent staining of nearly all cells. Similar results were seen with BT-549 cells (data not shown). DCIS specimens with areas of comedo-like necrosis showed markedly enhanced Epo and EpoR staining in the cells forming the viable rim around the necrotic center. Double staining of DCIS samples for Epo or EpoR and apoptotic nuclei via the Tunel method demonstrated Tunel positive apoptotic nuclei which were prominently localized in the border zone between necrotic and viable areas of DCIS specimens and only rarely amongst the viable cells which stain strongly for Epo and EpoR. Epo and EpoR staining of tumor vasculature demonstrated that blood vessels in the tumor samples showed immunoreactivity for Epo associated predominantly with the endothelium while EpoR staining was strongly seen in the endothelium and smooth muscle cells. All staining for EpoR and Epo was abolished upon pre-incubation of the respective antiserum with the control EpoR peptide or Epo peptide (not shown).

Example 9

Human Solid Cancers Express EpoR and Epo

Western blot analysis demonstrated strong expression of EpoR in several human cell lines including UT-7 erythrocytic leukemia cells, HEP3B hepatoma cells, Hela cervical carcinoma cells, SHSY5Y Neuroblastoma cells, U87 glioblastoma cells, U251 glioma cells, U373 Glioma cells, frozen specimen from ovarian cancer, frozen specimen from metastatic ovarian cancer, frozen sample of lung cancer. Expression of EpoR and Epo in medulloblastoma biopsy specimen demonstrated expression of EpoR and Epo in tumor vasculature. Staining for EpoR was associated with endothelium of arteriole and capillaries but not with smooth muscle. Epo staining was only faintly seen in endothelium.

Example 10

Epo and it Receptor EpoR are Prominently Expressed in Glioblastoma Multiforme Human glioma cell lines (ATCC) and normal human astrocytes (Clonetics) were cultured in Eagle's MEM medium supplemented with 10% fetal bovine serum, and 1% (v/v) penicillin/streptomycin. The cells were grown to 90% confluence in 10 cm culture dishes. For hypoxia treatment, the culture dishes were sealed in modulator incubator chamber, flushed with gas containing 1% oxygen, 5% carbon dioxide, 94% nitrogen for five minutes, and incubated at 37° C. for four to six hours. For desferrioxamine (DFX) treatment, the cells were cultured with same medium containing 156 mM DFX and incubated in cell culture incubator. Paraffin sections (5 μm) of the human GBMs were prepared and stained by immunohistochemistry methods as described previously (Acs et al. (2001) Cancer Res. 61, 3561-3565).

Figure 9B:
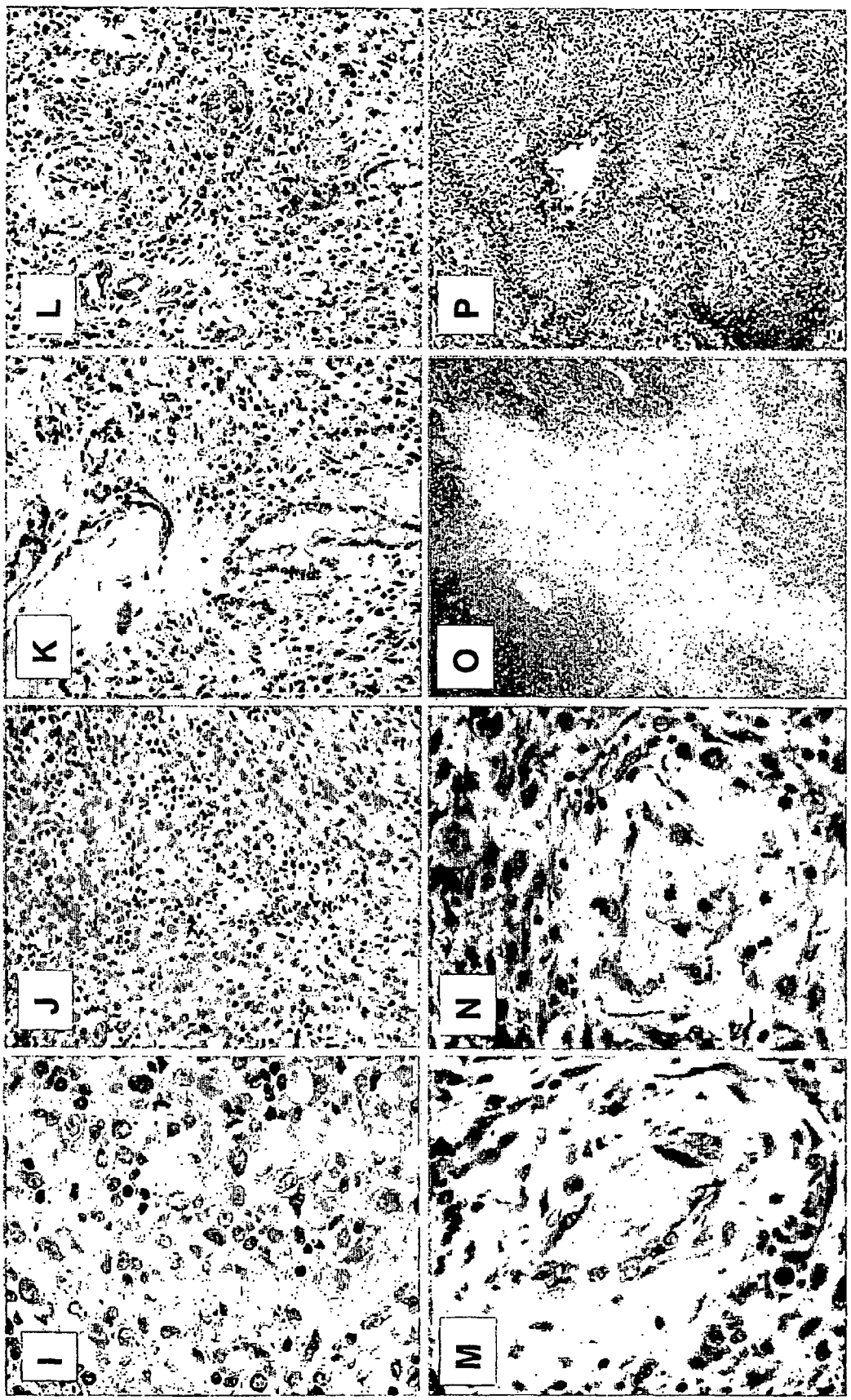
FIG. 9—Epo and it receptor EpoR are prominently expressed in Glioblastoma Multiforme. Immunohistochemical analysis of Epo and EpoR expression in clinical biopsies of gliobastoma multiforme shows strong association with malignant cells and tumor vasculature. (a) Granular cytoplasmic and golgi EpoR immunoreactivity in a GBM. An atypical mitotic figure lies in the center. (b) More diffuse and homogenous, cytoplasmic Epo immunoreactivity in the same GBM as depicted in (a). Hyperplastic, endothelial cells lining the blood vessel are also immunoreactive. (c) This GBM had alternating regions of tumor cells that were morphologically disparate and either immunonegative for Epo/EpoR (but reactive for other antibodies such as GFAP, not shown) or immunoreactive for both Epo and EpoR. (d) Epo (and EpoR, not shown) immunoreactive tumor cells infiltrating cerebral cortex. Reactive astrocytes in regions not infiltrated by tumor were immunonegative for Epo/EpoR (image not shown). (e and f) Epo (e) and EpoR (f) immunoreactivity in perivascular spindle cells of a GBM. (g and h) Epo (g) and EpoR (h) immunoreactivity in a gliosarcoma. (i and j) Epo (i) and EpoR (j) immunoreactivity in gemistocytic astrocytoma component of a GBM. (k and l) Vascular and tumoral immunoreactivity of Epo (k) and EpoR (l). (m and n) High power detail of the distribution of Epo (m) and EpoR (n) immunoreactivity in tumor vasculature. Endothelial cells, tumor cells and smooth muscle cells appear to be immunoreactive. (o) Non-palisaded necrosis within GBMs lacked Epo/EpoR (Epo shown) immunoreactivity in the central necrotic regions and lacked accentuation of immunoreactivity at the periphery of the necrotic region. (p) Palisaded necrosis in GBMs had accentuated Epo/EpoR (Epo shown) immunoreactivity in the viable tumor cells surrounding the necrotic region and within the central necrotic region itself. (400× original magnification was used to capture all frames, except for b, m and n, which were 1000× magnification, oil-immersion, and o and p, which were 200× magnification.)

Twenty five out of twenty five GBMs examined were immunoreactive for both Epo and EpoR (FIG. 9) 23 of 25 were strongly immunoreactive in the majority of tumor cells. In all cases, Epo and EpoR immunoreactivity coincided both in respects to region and cell type as best as could be determined. Two GBMs had moderately strong immunoreactivity in a minority (20-40%) of diffusely scattered, tumor cells. One GBM appeared to have a biclonal population of tumor cells in which one clone was negative for Epo/EpoR and one clone was immunonegative for Epo/EpoR. The two populations of tumor cells in the GBM also differed morphologically with the immunoreactive component being more pleomorphic, hyperchromatic and containing more gemistocytic cells. At the peripheral margins of tumor infiltration through the cerebral cortex, the GBM tumor cells retained Epo/EpoR immunoreactivity that was lacking in non-neoplastic, reactive brain parenchyma. The cytoplasm of gemistocytic tumor cells were strongly Epo/EpoR immunoreactive.

Example 11

EpoR Expression in Human Glioma Cells is Enhanced by Hypoxia

After the treatments to the cell culture dishes described in Example 10, the cells were washed once with 10 ml cold Dulbecco's phosphate-buffered saline (PBS), scraped into 1.5 ml of PBS on ice, and pelleted by centrifugation at 2,000 rpm for three minutes at 4° C. Cell pellets were washed once with 5 packed cell volumes of buffer A (10 mM Tris-HCl (pH 7.5), 1.5 mM magnesium chloride, 10 mM KCl), freshly supplemented with Complete, EDTA-free Protease Inhibitor Cocktail (Roche) and 2 mM dithiothreitol (DTT)), and resuspended in four packed cell volumes of buffer A. After incubation on ice for 10 min, cell suspension was homogenized with thirty strokes in a glass douncer (Wheaton) with type-b pestle. Nuclei were pelleted at 1,000 rpm for ten minutes and resuspended in four packed nuclear volumes of buffer C (20 mM Tris-HCl (pH 7.5), 0.42 M KCl, 1.5 mM magnesium chloride, 20% glycerol, freshly supplemented with Complete, EDTA-free Protease Inhibitor Cocktail (Roche) and 2 mM DTT), and rotated for thirty minutes at 4° C. After centrifugation at 1,400 rpm for thirty minutes, the nuclear extracts were aliquoted and stored at −80° C. Protein concentration was determined by the method of Bradford with a commercial kit (Bio-Rad) using bovine serum albumin as standard. HIF-1α protein was detected by immunoblot analysis. Twenty five to thirty μg of nuclear extracts were boiled for five minutes in 2× denaturing buffer, and loaded onto SDS-7% polyacrylamide gels. After transfer, membranes were blocked with 5% milk in TBST (10 mM Tris-HCl, 150 mM NaCl, 0.1% Tween, pH 7.8) for one and a half hours at room temperature and subsequently incubated with mouse monoclonal HIF-1α antibody (Transduction Labs) for two hours. The membranes were washed with TBST three times and incubated with horseradish peroxidase-conjugated secondary antibody. Then, the membranes were washed three times with TBST and analyzed by enhanced chemiluminescence (Pierce). Analysis of EpoR and phosphotyrosine immunoreactivity was performed as reported previously (Acs et al. (2001) Cancer Res. 61, 3561-3565).

Oligonucleotide probe was generated by 5' end labeling of the sense strand with gamma-[$^{32}$P]ATP (Dupont-NEN) and T4 polynucleotide kinase (Gibco-BRL), annealing to a tenfold excess of antisense strand, and purification by using NucTrap Probe Purification Column (Stratagene). Binding reactions were carried out in a total volume of 20 µl containing 7.0 µg of nuclear extract and 0.2 µg of calf thymus DNA in buffer Z (20 mM Tris-HCl (pH 7.5), 0.1 M KCl, 0.2 mM EDTA, 20% glycerol, freshly supplemented with 2 mM DTT, 0.4 mM PMSF and 1 mM $Na_3PO_4$). After preincubation for five minutes on ice, 1 µl probe (10,000 cpm) was added and the incubation was continued for an additional fifteen minutes. The reaction mixtures were loaded onto 5% nondenaturing polyacrylamide gels. Electrophoresis was performed at 200 volts in 0.3×TBE in cold room. Gels were vacuum dried and autoradiographed using Instant Inage System. The oligonucleotide probe from the erythropoietin enhancer region contained HIF-1 binding site (5'-GCCCTACGTGCT-GTCTCA-3' (SEQ ID NO: 1)).

Three human glioblastoma multiforme cells lines (U87, U251, U373) and normal human astrocytes (NHA) were examined for EpoR expression by western blotting. EpoR (66 kDa) was found to be prominently expressed by all three glioma cell lines but was only faintly seen in normal human astrocytes (FIG. 10A). While Epo is known to be induced by hypoxia, little is known regarding the sensitivity of EpoR expression to hypoxia. We explored the hypoxia-sensitivity of EpoR expression in U251 cells. When subjected to six-hour treatments of either hypoxia (1% oxygen) or 150 µM desferrioximine (DFX) U251 cells responded by dramatically upregulating the level of HIF-1α protein and HIF-1 gelshift activity indicating an intact and robust hypoxia-sensing mechanism. RT-PCR analysis for mRNA expression showed prominent induction of Epo by both hypoxia and DFX. EpoR mRNA was found to be expressed basally, but was less prominently induced by hypoxia, and was not induced by DFX. In contrast to this however immunoreactive EpoR protein levels were enhanced by both hypoxia and DFX.

Example 12

EPO can Stimulate Signaling Pathways in Human Gliomas

Using the Western blotting techniques described in Example 11 above, the immunoreactive EpoR expressed in human gliomas was further tested to see if it was functional. Cultured U251 cells were stimulated with recombinant human erythropoietin. A single dose of 10 U/ml rhEpo induced a prominent, rapid, and long lasting activation of tyrosine phosphorylation in several proteins as assessed by Western blotting (FIG. 11A). Tyrosine phosphorylation could also be elicited by an Epo-mimetic peptide (EMP) and by Epoetin-alfa, the clinically used form of Epo (FIG. 11B). Using phospho-specific antibodies, we also detected rhEpo stimulated Jak-2 and STAT-5 tyrosine phosphorylation as well as phosphorylation of Akt (FIG. 12C). These data establish that EpoR associated signaling pathways, which involve tyrosine and serine/threonine kinase cascades can be activated by Epo in human gliomas.

FIG. 13—EPO can Protect Glioma Cells from Toxicity of Chemotherapeutic Drugs and from Serum Withdrawal U251 cells were grown in 96-well culture dishes to approximately 85% confluence. Serum was withdrawn overnight and 10 µM Cisplatin was added for twenty-four hours. Cell survival was determined using the MTT assay and typically resulted in approximately 80% cell death. Control groups underwent similar serum withdrawal but no Cisplatin exposure. Where indicated rhEpo or Epoetin-alfa was added thirty minutes prior to the addition of cisplatin. Serum withdrawal studies involved assessment of cell survival forty-eight hours following change to serum-free media. Compared to serum-fed cells, this resulted in approximately 20% cell survival after forty-eight hours. Where indicated, Epoetin-alfa, tyrosine kinase inhibitors or PI3K inhibitors were added at the time of change to serum-free media. The Student's T-test was used to determine statistically significant differences between treatment groups.

To determine whether Epo could promote cell survival in human glioma cells, the effect of Epoetin-alfa on cisplatin toxicity was examined in U251 cells. Overnight treatment of U251 cells in serum-free media with 10 µM Cisplatin killed approximately 80% of the cells (FIG. 12). Epoetin-alfa was able to dose dependently reverse cisplatin toxicity. Similar results were seen with BCNU and Taxol (data not shown). These results demonstrate that Epo signaling can contribute to chemotherapy resistance in human glioma cells.

Prolonged serum withdrawal removes cell survival signals and leads to cell death. In U251 cells, approximately 80% cell death was observed forty-eight hours after serum withdrawal (FIG. 13). The cell death induced by serum withdrawal could be reduced by Epoetin-alfa, and this effect of Epoetin-alfa could be blocked by inhibitors of tyrosine kinases (genistein) or PI3 kinase (LY294002 and Wortmannin).

Although the present invention has been described in detail with reference to examples above, it is understood that various modifications can be made without departing from the spirit of the invention. Accordingly, the invention is limited only by the following claims. All cited patents, patent applications and publications referred to in this application are herein incorporated by reference in their entirety.

The invention claimed is:

1. A method of detecting a solid breast tumor in a patient comprising measuring erythropoietin or erythropoietin receptor expression in a patient sample isolated from breast tissue of the patient wherein an increased level of expression is indicative of the presence of a tumor.

2. The method of claim 1 wherein both erythropoietin and erythropoietin receptor expression are measured in the patient sample.

3. The method of claim 1, wherein the expression is determined by measuring the level of erythropoietin or the erythropoietin receptor polypeptide.

4. The method of claim 1, wherein the expression is determined by measuring the level of a nucleic acid encoding erythropoietin or the erythropoietin receptor.

5. The method of claim 4, wherein the nucleic acid is amplified using polymerase chain reaction.

6. The method of claim 5, wherein the nucleic acid is mRNA and the mRNA is reversed transcribed into DNA before amplification.

7. The method of claim 1, wherein the sample is isolated from the mammary gland.

8. The method of claim 1, wherein the tumor is selected from the group consisting of invasive lobular carcinoma, invasive ductal carcinoma and ductal carcinoma in situ.

* * * * *